US006444877B1

(12) United States Patent
Rottmann

(10) Patent No.: US 6,444,877 B1
(45) Date of Patent: Sep. 3, 2002

(54) LIQUIDAMBAR STYRACIFLUA AGAMOUS (LSAG) GENE

(75) Inventor: William Horn Rottmann, Summerville, SC (US)

(73) Assignee: Westvaco Corporation, New York, NY (US)

( * ) Notice: Subject to any disclaimer, the term of this patent is extended or adjusted under 35 U.S.C. 154(b) by 0 days.

(21) Appl. No.: 09/433,579

(22) Filed: Nov. 4, 1999

(51) Int. Cl.$^7$ .......................... C12N 5/04; C12N 15/29; C12N 15/82; C12N 15/90; A01H 5/00
(52) U.S. Cl. .................... 800/285; 435/320.1; 435/419; 435/468; 536/23.6; 536/24.5; 800/286; 800/298
(58) Field of Search ............................. 435/69.1, 320.1, 435/410, 419, 468; 536/23.6; 800/278, 286, 290, 295, 298

(56) References Cited

U.S. PATENT DOCUMENTS

| | | | |
|---|---|---|---|
| 5,477,002 A | 12/1995 | Tuttle et al. | 800/278 |
| 5,633,441 A | 5/1997 | De Greef et al. | 800/278 |
| 5,723,763 A | 3/1998 | Mariani et al. | 800/278 |
| 5,723,765 A | 3/1998 | Oliver et al. | 800/278 |
| 5,744,693 A | 4/1998 | Meyerowitz et al. | 800/278 |

FOREIGN PATENT DOCUMENTS

| | | | |
|---|---|---|---|
| WO | 8910396 | 11/1989 | C12N/5/00 |
| WO | 9205257 | 4/1992 | C12N/15/29 |
| WO | 9425613 | 11/1994 | C12N/15/82 |

OTHER PUBLICATIONS

Soon–Kee Sung et al., Molecular Cloning and Characterization of a MADS–Box cDNA Clone of the Fuji Apple. Plant Cell Physiol. 38(4), pp. 484–489.*

Liu, J. et al. (1999). "cDNA cloning and expression of a sweetgum gene that shows homology with *Arabidopsis AGAMOUS*," *Plant Science* 142:73–82.

Doctoral Thesis entitled "Structure and Expression of Two *Populus trichocarpa* Homologs of the floral Homeotic Gene AGAMOUS," by A.M. Brunner, Oregon State University, Jun. 5, 1998, pp 1–165 (with Abstract, Title, Contents).

Levy, Y.Y. et al. (1998). "The Transition to Flowering," *The Plant Cell* 10: 1973–1989.

TGERC Annual Report 1997–98, Oregon State University College of Forestry, pp. 1–45.

Sieburth, L.E. (1997). "Molecular Dissection of the AGAMOUS Control Region Shows That cis Elements for Spatial Regulation Are Located Intragenically," *The Plant Cell* 9:355–365.

Mizukami, Y. et al. (1996). "Functional Domains of the Floral Regulator AGAMOUS: Characterization of the DNA Binding Domain and Analysis of Dominant Negative Mutations," *The Plant Cell* 8:831–845.

Mol, J.N.M. et al. (1994). "Post–transcriptional Inhibition of Gene Expression: Sense and Antisense Genes,:" *Homologous Recombination and Gene Silencing in Plants*, J. Paszkowski (ed.), Kluwer Academic Publishers, Netherlands (pp. 309–334).

Taylor, L.P. et al. (1992). "Conditional Male Fertility in Chalcone Synthase–Deficient Petunia," *J. Hered.* 83:11–17.

* cited by examiner

*Primary Examiner*—Amy J. Nelson
*Assistant Examiner*—Ashwin D. Mehta
(74) *Attorney, Agent, or Firm*—Rothwell, Figg, Ernst & Manbeck, P.C.; Daniel B. Reece, IV; Terry B. McDaniel

(57) ABSTRACT

The present invention is directed to a gene and gene product of sweetgum (*Liquidambar styraciflua*), referred to herein as the LSAG gene, which is a homolog of the AGAMOUS gene. The LSAG gene is a flowering gene which is required for normal flower development and sweetgum fertility. The present invention is also directed to an LSAG promoter and/or enhancer and/or intron which can be used to prepare gene constructs and transgenic plants for tissue specific expression of the gene construct. The gene constructs and transgenic plants are further aspects of the present invention. Finally, the present invention is directed to methods to control flower development and hence assure sterility in transgenic sweetgum.

20 Claims, 1 Drawing Sheet

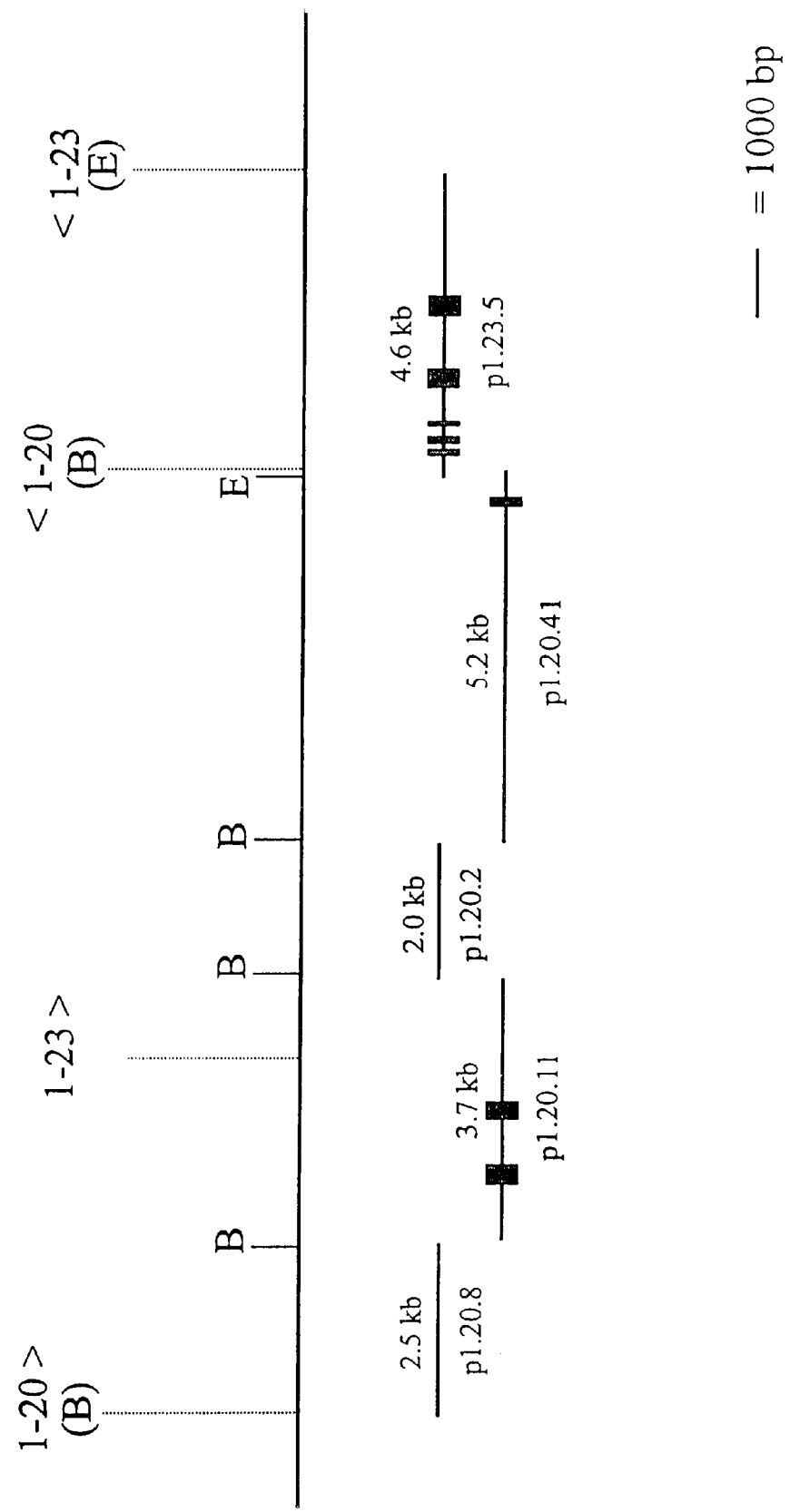

LIQUIDAMBAR STYRACIFLUA AGAMOUS (LSAG) GENE

BACKGROUND OF THE INVENTION

The present invention is directed to a gene and gene product of sweetgum (*Liquidambar styraciflua*), referred to herein as the LSAG gene, which is a homolog of the AGAMOUS gene (Meyerowitz et al. (1998)). The LSAG gene is a flowering gene which is required for normal flower development and sweetgum fertility. The present invention is also directed to an LSSAG promoter and/or enhancer and/or intron which can be used to prepare gene constructs and transgenic plants for tissue specific expression of the gene construct. The gene constructs and transgenic plants are further aspects of the present invention. Finally, the present invention is directed to methods to control flower development and hence assure sterility in transgenic sweetgum.

The publications and other materials used herein to illuminate the background of the invention or provide additional details respecting the practice, are incorporated by reference, and for convenience are respectively grouped in the appended List of References.

In order for transgenic plants to be grown outdoors, it is necessary that they not be harmful to the environment. For forest trees, one criterion is that they be reproductively sterile: unable to form flowers or gametes, and therefore unable to disperse pollen or seeds containing transgenes. This can be achieved by interfering with the function of genes required for normal reproductive development, as has been demonstrated by numerous mutations in Arabidopsis and other model species. However, the interference with such genes must not interfere with normal vegetative growth, especially in trees planted for production of timber or pulp.

There are many possible genes that can be used to control flowering. Research during the past two decades on several herbaceous species, especially the model species Arabidopsis, has produced a wealth of information about genes that are involved in the development of flowers (Levy and Dean (1998)). Although literally thousands of genes are activated during floral development, studies have focused on a few dozen "master control" genes that regulate transcription during the process. These genes were often first detected by the fact that mutations that inactivated them yielded grossly deformed flowers, or occasionally no flowers at all. The Arabidopsis gene AGAMOUS (AG) codes for a DNA-binding protein required for normal development of stamens and carpels. When it is mutated, petals are formed in the place of stamens and the carpels are replaced by nested sterile flowers. In situ hybridization studies have shown that the gene is transcribed only in floral meristems and primordia for stamens and carpels. The AGAMOUS protein shows sequence similarity with other regulatory proteins in the so-called MADS-box domains.

The methods of interfering with gene function in a transgenic plant include introducing a synthetic gene that causes sense or antisense suppression of the target gene (Taylor and Jorgensen (1992)). The suppression methods require substantial similarity between the target gene and the suppressing gene, greater than 80% nucleotide sequence identity (Mol et al. (1995)). Sweetgum is not closely related to the model plant systems from which most flowering genes have been isolated, and thus there do not seem to be any sequences that can reliably be used to suppress flower development in this species.

A gene encoding a dominant negative form of a protein essential for flowering may also be used to create a sterile plant. This has been reported in Arabidopsis for AGAMOUS (Mizukami et al. (1996)), but it is not known whether the dominant negative AGAMOUS gene will produce the same result in a heterologous species, such as sweetgum.

A further means of creating sterile trees is to introduce a transgene that specifically kills cells that are involved in floral development or production of gametes (genetic ablation). Numerous patents describe variations of genetic ablation for enabling controlled breeding of agricultural species, but they singly address either male or female sterility (Nasrallah et al. (1994); Tuttle and Crossland (1995); DeGreef et al. (1997); Mariani et al. (1998); Oliver et al. (1998)). One method includes delivering into the plant a gene encoding a cytotoxic substance associated with a male tissue specific promoter. Another method involves an antisense system in which a gene critical to fertility is identified and an antisense to the gene inserted in the plant. Some published patent applications also describe methods for complete sterility of plants (Mariani et al. (1988); Teasdale (1992); Bridges et al. (1990)). One method includes several cytotoxin encoding gene sequences, along with male tissue specific promoters and an antisense system. Another method uses "repressor" genes which inhibit the expression of another gene critical to male sterility. Additionally, it is yet to be convincingly demonstrated that these methods do not have a detrimental effect on vegetative development. Strauss and co-workers (1998) have seen marked reduction in growth of cottonwoods that contain several genetic ablation constructs whose expression was expected to be strictly limited to reproductive tissues.

An additional problem in genetic engineering of plants is the limited number of gene components such as introns or transcriptional terminators that are freely available for making synthetic genes. It has been noted that transgenes that have sequences duplicated elsewhere in the genome can be susceptible to transcriptional inactivation, possibly mediated by methylation of the repeated DNA. Therefore, multigene constructs run the risk of unstable expression if several of the genes contain repeated DNA because they share the same transcriptional terminator.

Thus, it is desired to identify sweetgum genes which are involved with flowering in order to derive promoter and/or enhancer and/or intron sequences for use in preparing transgenic plants or in order to interfere with normal flower development in transgenic sweetgum to produce sterile trees.

SUMMARY OF THE INVENTION

The present invention is directed to a gene and gene product of sweetgum (*Liquidambar styraciflua*), referred to herein as the LSAG gene, which is a homolog of the AGAMOUS gene, and to uses of the gene, gene product or parts of the gene.

In one aspect of the invention, the DNA and protein sequences are provided for sweetgum LSAG.

In a second aspect of the invention, constructs comprising at least a portion of an LSAG nucleic acid is provided for altering floral development. The constructs generally comprise a heterologous promoter, i.e., one not naturally associated with the LSAG gene, operably linked to the LSAG nucleic acid. The LSAG may be in sense or antisense orientation with respect to the promoter. Vectors containing the construct for use in transforming plant cells are also provided. Any plant cells can be transformed in accordance with the present invention. Preferred plant cells are plant cells of woody plants.

In a third apsect of the invention, plants having at least one cell transformed with the construct containing LSAG nucleic acid for altering floral development is provided. Such plants have a phenotype characterized by altered floral development. Preferred plants are woody plants.

In a fourth aspect of the invention, methods for producing plants having altered floral development are provided. The methods comprise the steps of transforming plant cells with a vector comprising at least a portion of an LSAG nucleic acid, regenerating plants from one or more of the transformed plant cells and selecting at least one plant exhibiting altered floral development.

In a fifth aspect of the invention, a promoter, an enhancer and an intron of the sweetgum LSAG gene are provided.

In a sixth aspect of the invention, gene constructs comprising the promoter and/or enhancer and/or intron of the LSAG gene and a heterologous gene are provided. Vectors containing these constructs are also provided. Plants having at least one cell containing these constructs are further provided by the invention.

DESCRIPTION OF THE DRAWING

The FIGURE shows the structure of the LSAG gene locus, as inferred from overlapping genomic DNA clones. The endpoints of the genomic clones are shown by dashed lines. Restriction enzyme sites are indicated: B=BamHI, E=EcoRI. The restriction sites shown in parentheses are sites that originate in the vector and were used in subcloning portions of the gene. The five restriction fragments that were subcloned, with their sizes and clone names, are indicated below the gene map. The rectangles placed on these fragments indicate exons.

SUMMARY OF THE SEQUENCES

SEQ ID NO:1 is the nucleotide sequence for the cDNA of LSAG. SEQ ID NO:2 is amino acid sequence for the LSAG polypeptide. SEQ ID NO:3 is nucleotide sequence of genomic LSAG.

DETAILED DESCRIPTION OF THE INVENTION

The present invention is directed to a gene and gene product of sweetgum (*Liquidambar styraciflua*), referred to herein as the LSAG gene, which is a homolog of the AGAMOUS gene. The LSAG gene is a flowering gene which is required for normal flower development and sweetgum fertility. The present invention is also directed to an LSAG promoter and/or enhancer and/or intron which can be used to prepare gene constructs and transgenic plants for tissue specific expression of the gene construct. The gene constructs and transgenic plants are further aspects of the present invention. Finally, the present invention is directed to methods to control flower development and hence assure sterility in transgenic sweetgum.

LSAG cDNA (SEQ ID NO:1) and LSAG gene (SEQ ID NO:3) consist of sequences specific to sweetgum that bear similarity to the AGAMOUS gene of Arabidopsis. There is no evidence for other genes very similar to LSAG in the sweetgum genome, so it is a perfect candidate for preventing both male and female flower development in sweetgum. Despite the similarities that AGAMOUS and its homologs from other species have to LSAG, it does not appear that such homologs would be useful for producing suppression of the sweetgum gene. In the most conserved regions of the protein coding sequence, where the greatest similarity between species exists, AGAMOUS shares enough sequence identity with other regulatory proteins (so-called MADS-box genes) that it might also suppress these other regulatory proteins in addition to the intended target, LSAG, and lead to developmental abnormalities in vegetative growth. In less conserved regions, such as the carboxyl-region of the coding sequence and the 3'-untranslated region, AGAMOUS and LSAG share less than the approximately 80% sequence identity needed for suppression.

Despite the fact that much can be predicted based on similarity to AGAMOUS and other genes, the LSAG cDNA and gene are novel sequences. In particular, several portions of the LSAG gene do not resemble sequences from related genes. Knowledge of the sequence of the gene enables any portion of the gene to be inserted into a transgene construct through well-characterized procedures. Following are some uses of the LSAG cDNA and gene sequences or portions of them.

It is generally the case that promoter sequences do not show sequence similarities except for homologous genes from very closely related species, or for short motifs that must be found by experimentation. In keeping with this observation, the promoter region of the LSAG gene bears no noticeable similarity to the known promoters of other members of the gene family. Only the Arabidopsis (GenBank accession AL021711) and two Populus (GenBank accessions AF052570 and AF052571) promoter sequences have been published for the AGAMOUS gene family. The promoter of the LSAG gene is a new sequence that can be used for directing expression of a chosen sequence in the developing male and female organs of a flowering plant. It appears that the promoter of AGAMOUS does not direct flower-specific gene expression on its own, but may need to be modified, for example by the addition of sequences from the second intron of the AGAMOUS gene (Sieburth and Meyerowitz (1997)). Similarly, it appears that the LSAG promoter may also require modification by addition of enhancer sequences from the LSAG second intron for chimeric genes to be transcribed in a floral-specific manner.

As described in further detail herein, the LSAG gene can be used to prevent normal male and female flowering to render trees reproductively sterile. Briefly, two techniques for using the LSAG gene for this purpose are antisense or sense suppression to decrease the level of expression of the endogenous LSAG gene. For this use, the carboxyl-region of the coding sequence and the 3'-untranslated region would be preferred because these would not be likely to cause deleterious effects through suppression of other MADS-box genes. A third technique is to use the regulatory sequences of LSAG to direct expression of a lethal gene product specifically in flower tissues (genetic ablation). In each of these cases, it is desired to also include a system which could be used to selectively deactivate the sterility gene to render the trees fertile for production of pollen or setting of seed.

The transcription termination region of the LSAG gene can be used to end transcription from a chimeric gene. The transcription termination region was determined by analysis of multiple LSAG cDNAs which all ended in the same region, indicating that this region acts efficiently and can reliably be used in making chimeric genes. All but two cDNAs examined ended at position 15993 of SEQ ID NO:3, while the remainder ended at position 16009. The sequence of the transcription termination region of the LSAG gene would not be predicted merely by knowing the sequences of other homologous genes.

Some chimeric genes may require an intron. Several reports have indicated that introns can enhance gene expression (Norris et al. (1993); Rethmeier et al. (1996)). Additionally, the presence of an intron will prevent expression of a reporter gene or selectable marker gene in the bacterial cells needed for manipulating DNA, and can be used as an aid for selecting transformed cells or tissue. In addition, since the presence of an intron can prevent translation of the RNA to a functioning product in bacterial cells (Maas et al. (1997)), its presence can strongly decrease the possibility that inactivating mutations will be introduced into a toxic gene. The LSAG gene possesses several short introns that may be amplified by PCR and inserted into genetic ablation constructs for this purpose.

Definitions

The present invention employs the following definitions, which are, where appropriate, referenced to LSAG.

"Altered floral development" or "modified floral phenotype" refers to a physical modification in the structure of a plant's reproductive tissue as compared to the parent plant from which the plant having the modified phenotype is obtained. Macroscopic alterations may include changes in the size, shape, number or location of reproductive organs. Microscopic alterations may include changes in the types or shapes of cells that make up the reproductive structures. Such modified floral phenotypes can be uniform throughout the plant and typically arise when each of the cells within the plant contain cells transformed with a vector comprising at least a portion of the LSAG nucleic acid. Such plants are sometimes referred to as transgenic plants. The phenotype produced in a particular plant is dependent upon the design of the vector used to produce it. Thus, the vector can be designed to transcribe a nucleic acid which encodes at least a portion of the LSAG protein. In such cases, the LSAG protein so produced is capable of conferring a particular phenotype based on the presence of that protein within the cell. Alternatively, the vector can be constructed such that transcription results in the formation of a transcript which is capable of hybridizing with an RNA transcript of an endogenous LSAG or other AGAMOUS homolog gene. This approach employs the well known antisense technology and results in a modulation in the phenotypic effect of the endogenous LSAG genes. Such modulation of the endogenous LSAG gene can also potentially be obtained by using the sense strand of the LSAG gene to cause sense suppression of the endogenous LSAG alleles as well as the LSAG gene introduced in the vector. The production of a plant containing such a phenotype is contemplated based upon the sense suppression observed in *Petunia hybrida* as set forth in PCT Publication WO 90/12084. The vector may comprise the LSAG promoter regulating transcription of a gene encoding a protein that interferes will cell growth. In such cases, the altered floral development exhibited may be severe atrophy or loss of reproductive structures.

"Amplification of polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al. (1990) (for PCR); Wu and Wallace (1989) (for LCR); U.S. Pat. Nos. 5,270,184 and 5,455,166 and Walker et al. (1992) (for SDA); Spargo et al. (1996) (for thermophilic SDA) and U.S. Pat. No. 5,409,818, Fahy et al. (1991) and Compton (1991) (for 3SR and NASBA). Reagents and hardware for conducting PCR are commercially available. Primers useful to amplify sequences from the LSAG region are preferably complementary to, and hybridize specifically to sequences in the LSAG region or in regions that flank a target region therein. LSAG sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf et al. (1986).

"Analyte polynucleotide" and "analyte strand" refer to a single- or double-stranded polynucleotide which is suspected of containing a target sequence, and which may be present in a variety of types of samples, including biological samples.

"Binding partner" refers to a molecule capable of binding a ligand molecule with high specificity, as for example, complementary polynucleotide strands or an enzyme and its inhibitor. In general, the specific binding partners must bind with sufficient affinity to immobilize the analyte copy/complementary strand duplex (in the case of polynucleotide hybridization) under the isolation conditions. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. Further binding partners can be identified using, e.g., the two-hybrid yeast screening assay as described herein.

A "biological sample" refers to a sample of tissue or fluid suspected of containing an analyte polynucleotide or polypeptide from a plant including, but not limited to, e.g., pollen, ovules, cells, organs, tissue and samples of in vitro cell culture constituents.

"Encode". A polynucleotide is said to "encode" a polypeptide if, in its native state or when manipulated by methods well known to those skilled in the art, it can be transcribed and/or translated to produce the MRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native sweetgum sequence or protein, e.g., ribosomes, polymerases, many other sweetgum genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"LSAG allele" refers, respectively, to normal alleles of the LSAG locus as well as alleles of LSAG having variations, isolated from plants or produced in accordance with the present invention.

"LSAG locus", "LSAG gene", "LSAG nucleic acids" or "LSAG polynucleotide" each refer to polynucleotides, all of which are in the LSAG region, respectively, that are likely to be expressed in normal tissue and involved in sweetgum flower development. The LSAG locus is intended to include coding sequences, intervening sequences and regulatory elements (e.g., promoters and enhancers) controlling transcription and/or translation. The LSAG locus is intended to include all allelic variations of the DNA sequence.

These terms, when applied to a nucleic acid, refer to a nucleic acid which encodes a sweetgum LSAG polypeptide, fragment, homolog or variant, including, e.g., protein fusions or deletions. The nucleic acids of the present invention will possess a sequence which is either derived from, or substantially similar to, a natural LSAG-encoding gene or one having substantial homology with a natural LSAG-encoding gene or a portion thereof. The term LSAG nucleic acid is sometimes used to refer to the sense and antisense strands of the LSAG gene collectively.

The LSAG gene or nucleic acid includes normal alleles of the LSAG gene, respectively, including silent alleles having no effect on the amino acid sequence of the LSAG polypeptide as well as alleles leading to amino acid sequence variants of the LSAG polypeptide that do not substantially affect its function. These terms also include alleles having one or more mutations which adversely affect the function of the LSAG polypeptide. A mutation may be a change in the LSAG nucleic acid sequence which produces a deleterious change in the amino acid sequence of the LSAG polypeptide, resulting in partial or complete loss of LSAG function, respectively, or may be a change in the nucleic acid sequence which results in the loss of effective LSAG expression or the production of aberrant forms of the LSAG polypeptide.

The LSAG nucleic acid may be that shown in SEQ ID NO:1 or SEQ ID NO:3 or it may be an allele as described above or a variant or derivative differing from that shown by a change which is one or more of addition, insertion, deletion and substitution of one or more nucleotides of the sequence shown. Changes to the nucleotide sequence may result in an amino acid change at the protein level, or not, as determined by the genetic code.

Thus, nucleic acid according to the present invention may include a sequence different from the sequence shown in SEQ ID NO:1 or SEQ ID NO:3 yet encode a polypeptide with the same amino acid sequence as shown in SEQ ID NO:2. That is, nucleic acids of the present invention include sequences which are degenerate as a result of the genetic code. On the other hand, the encoded polypeptide may comprise an amino acid sequence which differs by one or more amino acid residues from the amino acid sequence shown in SEQ ID NO:2. Nucleic acid encoding a polypeptide which is an amino acid sequence variant, derivative or allele of the amino acid sequence shown in SEQ ID NO:2 is also provided by the present invention.

The LSAG gene, respectively, also refers to (a) any DNA sequence that (i) hybridizes to the complement of the DNA sequences that encode the amino acid sequence set forth in SEQ ID NO:2 under highly stringent conditions (Ausubel et al. (1992)) and (ii) encodes a gene product functionally equivalent to LSAG, or (b) any DNA sequence that (i) hybridizes to the complement of the DNA sequences that encode the amino acid sequence set forth in SEQ ID NO:2 under less stringent conditions, such as moderately stringent conditions (Ausubel et al. (1992)) and (ii) encodes a gene product functionally equivalent to LSAG. The invention also includes nucleic acid molecules that are the complements of the sequences described herein.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the LSAG region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it may also be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons(15 nucleotides), more usually at least about 7–15 codons, and most preferably, at least about 35 codons. One or more introns may also be present. This number of nucleotides is usually about the minimal length required for a successful probe that would hybridize specifically with an LSAG-encoding sequence. In this context, oligomers of as low as 8 nucleotides, more generally 8–17 nucleotides, can be used for probes, especially in connection with chip technology.

Techniques for nucleic acid manipulation are described generally, e.g., in Sambrook et al. (1989) or Ausubel et al. (1992). Reagents useful in applying such techniques, such as restriction enzymes and the like, are widely known in the art and commercially available from such vendors as New England BioLabs, Boehringer Mannheim, Amersham, Promega, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, a "portion" of the LSAG locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides. The present invention includes all novel nucleic acids having at least 8 nucleotides derived from SEQ ID NO:1 or SEQ ID NO:3, their complement or functionally equivalent nucleic acid sequences. The present invention does not include nucleic acids which exist in the prior art. That is, the present invention includes all nucleic acids having at least 8 nucleotides derived from SEQ ID NO:1 or SEQ ID NO:3 with the proviso that it does not include nucleic acids existing in the prior art, such as disclosed in published sequences for the AGAMOUS gene or its homologs.

"LSAG protein" or "LSAG polypeptide" refers to a protein or polypeptide encoded by the LSAG locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native LSAG sequence, preferably in excess of about 90%, and more preferably at least about 95% homologous. Also included are proteins encoded by DNA which hybridize under high or low stringency conditions, to LSAG-encoding nucleic acids and closely related polypeptides or proteins retrieved by antisera to the LSAG protein(s).

The LSAG polypeptide may be that shown in SEQ ID NO:2 which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the LSAG polypeptide. Such polypeptides may have an amino acid sequence which differs from that set forth in SEQ ID NO:2 by one or more of addition, substitution, deletion or insertion of one or more amino acids. In one embodiment, these variant polypeptides have a function similar to LSAG such that they can be used to restore fertility or used in place of homologous genes. In a second embodiment, these variant peptides do not retain the LSAG function such that they can be used as a dominant negative.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with the LSAG polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (Kyte and Doolittle (1982)). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

"Probes". Probes for LSAG alleles may be derived from the sequences of the LSAG region, its cDNA, functionally equivalent sequences, or the complements thereof. The probes may be of any suitable length, which span all or a portion of the LSAG region, and which allow specific hybridization to the region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al. (1989) or Ausubel et al. (1992). Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 kb, usually fewer than about 1.0 kb, from a polynucleotide sequence encoding LSAG are preferred as probes. This definition therefore includes probes of sizes 8 nucleotides through 9000 nucleotides. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30, 38, 50, 72, 121, etc., nucleotides), or probes having more than 500 nucleotides. The probes may also be used to determine whether mRNA encoding LSAG is present in a cell or tissue. The present invention includes all novel probes having at least 8 nucleotides derived from SEQ ID NO:1 or SEQ ID NO: 3, its complement or functionally equivalent nucleic acid sequences. The present invention does not include probes which exist in the prior art. That is, the present invention includes all probes having at least 8 nucleotides derived from SEQ ID NO:1 or SEQ ID NO:3, with the proviso that they do not include probes existing in the prior art.

Similar considerations and nucleotide lengths are also applicable to primers which may be used for the amplification of all or part of the LSAG gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 9000. The primers may also be used to determine whether mRNA encoding LSAG is present in a cell or tissue. The present invention includes all novel primers having at least 8 nucleotides derived from the LSAG locus for amplifying the LSAG gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein purification" refers to various methods for the isolation of the LSAG polypeptides from other biological material, such as from cells transformed with recombinant nucleic acids encoding LSAG, and are well known in the art. For example, such polypeptides may be purified by immunoaffinity chromatography employing, e.g., antibodies prepared against LSAG using conventional techniques. Various methods of protein purification are well known in the art, and include those described in Deutscher (1990) and Scopes (1982).

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

A LSAG protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide", as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to join together nucleic acid segments of desired functions to generate a desired combination of functions. Alternatively, it is performed to replace a codon with a redundant codon encoding the same or a conservative amino acid, while typically introducing or removing a sequence recognition site.

"Regulatory sequences" refers to those sequences normally within 100 kb of the coding region of a locus, but they may also be more distant from the coding region, or they may be located within introns of the gene, which affect the expression of the gene (including transcription of the gene, and translation, splicing, stability or the like of the messenger RNA).

"Substantial homology, similarity or identity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Identity means the degree of sequence relatedness between two polypeptide or two polynucleotides sequences as determined by the identity of the match between two strings of such sequences. Identity can be readily calculated. While there exist a number of methods to measure identity between two polynucleotide or polypeptide sequences, the term "identity" is well known to skilled artisans (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987;

and Sequence Analysis Primer, Gribskov, M. and Devereux, J., eds., M Stockton Press, New York, 1991). Methods commonly employed to determine identity between two sequences include, but are not limited to those disclosed in *Guide to Huge Computers,* Martin J. Bishop, ed., Academic Press, San Diego, 1994, and Carillo, H., and Lipman, D. (1988). Preferred methods to determine identity are designed to give the largest match between the two sequences tested. Such methods are codified in computer programs. Preferred computer program methods to determine identity between two sequences include, but are not limited to, GCG program package (Devereux et al. (1984), BLASTP, BLASTN, FASTA (Altschul et al. (1990); Altschul et al. (1997)).

Alternatively, substantial homology or (similarity or identity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa (1984). The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid and can be determined by techniques well known in the art. See, e.g., Wetmur and Davidson (1968).

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705, as well as the software described above with reference to nucleic acid homology. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type LSAG nucleic acid or wild-type LSAG polypeptide. The modified polypeptide will be substantially homologous to the wild-type LSAG polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type LSAG polypeptide. Alternatively, the similarity of function (activity) of the modified polypeptide may be higher than the activity of the wild-type LSAG polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type LSAG gene function produces the modified protein described above.

A polypeptide "fragment", "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase. support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe, a primer or an antisense will form a stable hybrid under desired conditions.

The practice of the present invention employs, unless otherwise indicated, conventional techniques of chemistry, molecular biology, microbiology, recombinant DNA and genetics. See, e.g., Maniatis et al. (1982); Sambrook et al. (1989); Ausubel et al. (1992); Glover (1985); Anand (1992); Guthrie and Fink (1991); Weissbach and Weissbach (1986); Zaitlin et al. (1985) and Gelvin et al. (1990).

Methods of Use: Preparation of Recombinant or Chemically Synthesized Nucleic Acids: Vectors, Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. Purification of nucleic acids produced by the methods of the present invention are described, e.g., in Sambrook et al. (1989) or Ausubel et al. (1992).

The polynucleotides of the present invention may also be produced by chemical synthesis, e.g., by the phosphoramidite method described by Beaucage and Caruthers (1981) or the triester method according to Matteucci and Caruthers (1981) and may be performed on commercial, automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors may be prepared by means of standard recombinant techniques well known in the art and discussed, for example, in Sambrook et al. (1989) or Ausubel et al. (1992).

An appropriate promoter and other necessary vector sequences will be selected so as to be functional in the host, and may include, when appropriate, those naturally associated with the LSAG gene. Examples of workable combinations of cell lines and expression vectors are described in Sambrook et al. (1989) or Ausubel et al. (1992); see also, e.g., Metzger et al. (1988). Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al. (1978)) or promoters derived from murine Molony leukemia virus, mouse tumor virus, avian sarcoma viruses, adenovirus II, bovine papilloma virus or polyoma. Insect promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, Cold Spring Harbor, N.Y. (1983). See also, e.g., U.S. Pat. Nos. 5,691,198; 5,735,500; 5,747,469 and 5,436,146. Plant control sequences are disclosed in, for example, U.S. Pat. Nos. 5,106,739; 5,322,938; 5,710,267; 5,268,526 and 5,290,294.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that (a) confer resistance to antibiotics or other toxic substances, e.g. ampicillin, neomycin, methotrexate, etc., (b) complement auxotrophic deficiencies, or (c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well known methods, e.g., by injection (see, Kubo et al. (1988)), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a viral genome); and other methods. See generally, Sambrook et al. (1989) and Ausubel et al. (1992). The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the LSAG nucleic acid or portions thereof in vectors or other expression vehicles in compatible prokaryotic or eukaryotic host cells. The most commonly used prokaryotic hosts are strains of *Escherichia coli,* although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.) (1979). Examples of commonly used mammalian host cell lines are VERO and HeLa cells, Chinese hamster ovary (CHO) cells, and W138, BHK, and COS cell lines, although it will be appreciated by the skilled practitioner that other cell lines may be appropriate, e.g., to provide higher expression, desirable glycosylation patterns, or other features. An example of a commonly used insect cell line is SF9.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of LSAG polypeptides.

The probes and primers based on the LSAG gene sequence disclosed herein are used to identify gene sequences and proteins homologous to LSAG in other species. These gene sequences and proteins are used in the diagnostic/prognostic, such as predicting reproductive phenotype in transgenic plants and genetic engineering methods described herein for the species from which they have been isolated.

Methods of Use: Controlling Reproductive Development of Sweetgum

The vectors used to transform plant cells comprise an LSAG nucleic acid or portion thereof which is capable of hybridizing with the endogenous LSAG gene of sweetgum. Thus, such nucleic acids include the positive strand of the LSAG gene encoding all or part of a protein and the antisense strand. In either case, the LSAG nucleic acid or its transcript is capable of hybridizing with and endogenous LSAG gene as defined herein or its transcript. The conditions under which such hybridization occurs include the physiological or equivalent conditions found within plant cells including that found in the nucleus and cytoplasm as well as standard in vitro conditions normally used by the skilled artisan to determine sequence homology as between two nucleic acids. Such in vitro conditions range from moderate (about 5×SSC at 52° C.) to high (about 0.1×SSC at 65° C.) stringency conditions.

The LSAG gene is used to construct sense or antisense vectors for transforming plant cells. The construction of such vectors is facilitated by the use of a binary vector which is capable of manipulation and selection in both a plant and a convenient cloning host such as a prokaryote. Thus, such a binary vector can include a kanamycin or herbicide resistance gene for selection in plant cells and an actinomycin resistance gene for selection in a bacterial host. Such vectors, of course, also contain an origin of replication appropriate for the prokaryotic host used, and preferably at least one unique restriction site or a polylinker containing unique restriction sites to facilitate vector construction.

In one embodiment, a constitutive promoter is used to drive expression of the LSAG nucleic acid within at least a portion of the reproductive tissues in the recipient plant. A particularly preferred promoter is the cauliflower mosaic virus 35S transcript promoter (Guilley et al. (1982); Odell et al. (1985), and Saunders et al. (1987)). However, other constitutive promoters can be used, such as the α-1 and β-1 tubulin promoters (Silflow et al. (1987)) and the histone promoters (Chaubet et al. (1987)). Other promoters which can be used include the promoters for the AGAMOUS gene, the APETALA2 gene, the APETALA3 gene and the PISTILLATA gene. Since these latter genes are associated with differentiation of reproductive tissue, such promoters are expected to provide tissue and temporal specificity to the expression of the LSAG nucleic acid. Additional DNA sequences that direct reproductive gene expression are the pistil-specific or anther-specific promoter described by Nasrallah et al. (1994). In addition to the forgoing promoters, meristem-specific promoters can be used. An example of such a promoter is PROLIFERA (Springer et al. (1995)).

In a further embodiment of the invention, the vector used to transform the sweetgum plant cell to produce a sweetgum having an altered floral phenotype is constructed to target the insertion of the LSAG nucleic acid into an endogenous promoter within a plant cell. One type of vector which can be used to target the integration of an LSAG nucleic acid to an endogenous promoter comprises a positive-negative selection vector analogous to that set forth by Monsour et al. (1988), which describes the targeting of exogenous DNA to a predetermined endogenous locus in mammalian ES cells. Similar constructs utilizing positive and negative selection markers functional in plant cells can be readily designed based upon the identification of the endogenous plant promoter and the sequence surrounding it (Kempin et al. (1997)). When such an approach is used, it is preferred that a replacement-type vector be used to minimize the likelihood of reversion to the wild-type phenotype.

The vectors of the invention are designed such that the promoter sequence contained in the vector or the promoter sequence targeted in the plant cell genome are operably linked to the nucleic acid encoding the LSAG gene. When the positive strand of the LSAG gene is used to express all or part of the LSAG protein, the term "operably linked" means that the promoter sequence is positioned relative to the coding sequence of the agamous nucleic acid such that RNA polymerase is capable of initiating transcription of the LSAG nucleic acid from the promoter sequence. In such embodiments it is also preferred to provide appropriate ribosome binding sites, transcription initiation and termination sequences, translation initiation and termination sequences and polyadenylation sequences to produce a functional RNA transcript which can be translated into LSAG protein. When an antisense orientation of the LSAG nucleic acid is used, all that is required is that the promoter be operably linked to transcribe the LSAG antisense strand. Thus, in such embodiments, only transcription start and termination sequences are needed to provide an RNA transcript capable of hybridizing with the MRNA or other RNA transcript from the endogenous LSAG gene. In addition to promoters, other expression regulation sequences, such as enhancers, can be added to the vector to facilitate the expression of LSAG nucleic acid in vivo.

Alternatively, sterility is induced by the expression of a lethal gene product specifically in flower tissues (genetic ablation). In this embodiment, a vector is constructed which contains the regulatory sequences of the LSAG gene (or other floral specific gene) and a coding sequence of the lethal gene product. Examples of lethal gene products include, but are not limited to, RNases, such as RNase T1 (which degrades RNA molecules by hydrolyzing the bond after any guanine residue), RNase $T_2$, RNase Rh and Bamase; DNases such as an endonuclease, such as EcoRI; proteases, such as a papain (e.g., papain zymogen or papain active protein); lipases; lipid peroxidases; plant cell wall inhibitors; and bacterial toxins, such as the A-fragment of diphtheria toxin or botulin.

Once a vector is constructed, the transformation of plants can be carried out in accordance with the invention by essentially any of the various transformation methods known to those skilled in the art of plant molecular biology. Such methods are generally described in Wu and Grossman (1987). As used herein, the term "transformation" means the alteration of the genotype of a plant cell by the introduction of a nucleic acid sequence. Particular methods for transformation of plant cells include the direct microinjection of the nucleic acid into a plant cell by use of micropipettes. Alternatively, the nucleic acid can be transferred into a plant cell by using polyethylene glycol (Paszkowski et al. (1984)). Other transformation methods include electroporation of protoplasts (Fromm et al. (1985); infection with a plant specific virus, e.g., cauliflower mosaic virus (Hohn et al. (1982)) or use of transformation sequences from plant specific bacteria such as Agrobacterium tumefaciens, e.g., a Ti plasmid transmitted to a plant cell upon infection by Agrobacterium tumefaciens (Horsch et al. (1984); Fraley et al. (1983)). Alternatively, plant cells can be transformed by introduction of nucleic acid contained within the matrix or on the surface of small beads or particles by way of high velocity ballistic penetration of the plant cell (Klein et al. (1987)). The nucleic acid introduced with ballistics may be a chimeric oligonucleotide designed to target a small number of mutated bases to a selected segment of the endogenous LSAG gene (Beetham et al. (1999)). A small number of mutated bases can also be introduced into a selected segment of the endogenous LSAG gene using homologous recombination (Kempin et al. (1997)).

After the vector is introduced into a plant cell, selection for successful transformation is typically carried out prior to regeneration of a plant. Such selection for transformation is not necessary, but facilitates the selection of regenerated plants having the desired phenotype by reducing wild-type background. Such selection is conveniently based upon the antibiotic resistance and/or herbicide resistance genes which may be incorporated into the transformation vector.

Practically all plants can be regenerated from cultured cells or tissues. As used herein, the term "regeneration" refers to growing a whole plant from a plant cell, a group of plant cells or a plant part. The methods for plant regeneration are well known to those skilled in the art. For example, regeneration from cultured protoplasts is described by Evans et al. (1983); and H. Binding (1985). When transformation is of an organ part, regeneration can be from the plant callus, explants, organs or parts. Such methods for regeneration are also known to those skilled in the art. See, e.g., Wu and Grossman (1987); Weissbach and Weissbach (1986); and Klee et al. (1987).

Once plants have been regenerated, one or more plants are selected based upon a change in the floral phenotype. Such selection can be by visual observation of gross morphological changes in floral structure, by observation in a change in inflorescence or by observation in changes in microscopic floral structure, e.g., by electron microscopy and the like.

In those cases wherein a dominant phenotype is conferred upon transformation with a vector containing an LSAG nucleic acid, the alteration in floral development can result in a sterile plant. In such cases, the plant can be propagated asexually by the taking of cuttings or by tissue culture techniques to produce multiple identical plants. Alternatively, the alteration in floral development can be ablated when desired as further described herein.

When the transformed plant is characterized by a recessive phenotype, e.g., when an antisense construct is used which is insufficient to confer the desired phenotype or which confers an intermediate phenotype which does not result in a sterile plant, such transformed plants can be inbred to homozygosity to obtain the desired phenotype. Such plants may then be asexually propagated or the alteration in floral development can be ablated when desired as further described herein.

Either antisense or co-suppression mechanisms using LSAG nucleic acids can result in abnormal flowers, including the double flower (extra petals) phenotype in many species. Double flowers would not be expected in sweetgum, because this species produces flowers that totally lack petals (Schmitt (1964)). This same antisense or co-suppression mechanism can also result in complete male and female sterility. In addition, plants having such modified floral phenotypes can be used as model systems for further study of the formation and differentiation of reproductive tissue in plants.

Although one object of the invention is to produce transgenic sweetgum which is sterile for purposes of environmental release, it may be desired to occasionally provide for sexual reproduction of such transgenic sweetgum to provide a source of seed of the transgenic sweetgum for further production of new transgenic sweetgum varieties. In one aspect, it is desired to inactivate the sweetgum sterility caused by the above sense or antisense suppression in order to restore temporary fertility. Knowledge of the sequence of the 3'-untranslated region of LSAG enables inactivation of the endogenous gene in sweetgum through antisense or sense suppression, while allowing a AGAMOUS gene homolog from another species to be present simultaneously and remain functional as a restorer of fertility. In a second aspect, it is desired to inactivate the sweetgum sterility caused by the above genetic ablation, i.e. lethal gene product, in order to restore temporary fertility. In the case of a gene based on Barnase, expression of Barstar in the target tissues would restore fertility. In the general case, knowledge of the the nucleotide sequence encoding the lethal gene product enables inactivation of the lethal gene through antisense or sense suppression as a restorer of fertility. In the preferred embodiment, an inducible promoter can be used to drive expression of the restorer gene. A chemically inducible promoter, preferably one inducible by a compound that is not ordinarily found in the outdoor environment, such as a promoter containing a glucocorticoid-responsive element or a tetracycline operator, would be suitable. A gene for an exogenous regulatory protein, such as the glucocorticoid receptor or the Tet repressor would also be included in the restorer construct.

Methods of Use: Regulatory Sequences for Plant Transformation

In another aspect of the invention, a DNA molecule is provided which comprises regulatory sequences of the LSAG gene operably linked to one or more genes or antisense DNA. The regulatory sequences may be the LSAG promoter, intron sequences or termination sequences. The LSAG promoter begins at the start of exon 1 in SEQ ID NO:3 and extends upstream by about 2 kb of sequence. At least one regulatory sequence is found in intron 2. The gene or antisense DNA imparts an agronomically useful trait or selectable marker to a transformed plant. In one embodiment, the DNA molecule include the LSAG promoter and an additional nucleotide sequence that influences gene expression. Examples of nucleotide sequences that influence the regulation of heterologous genes include enhancers or activating regions, such as those derived from CaMV 35S, opine synthase genes or other plant genes (U.S. Pat. Nos. 5,106,739; 5,322,938; 5,710,267; 5,268,526; 5,290,294). In a second embodiment, a promoter such as CaMV 35S promoter is used with regulatory sequences, such as intron sequences or termination sequences of LSAG. In a third embodiment, an intron of LSAG is inserted into a DNA molecule which will be used to transform plants as a means to easily select or identify transformed tissue in the presence of transforming bacteria. In a fourth embodiment, the DNA molecule is part of an expression vector. In a fifth embodiment, the DNA molecule is part of a transformation vector.

In an additional aspect of the present invention, transformed plant cells and tissues, transformed plants and seeds of transformed plants are provided. The expression of the gene or antisense DNA is regulated by the LSAG regulatory sequences and additional regulatory sequences, if present.

By means of the present invention, agronomic genes and selectable marker genes can be operably linked to LSAG regulatory sequences and expressed in transformed plants. More particularly, plants can be genetically engineered to express various phenotypes of agronomic interest. Such genes included, but are not limited to, those described herein.

1. Genes that Confer Resistance or Tolerance to Pests or Disease (A) Plant disease resistance genes. Plant defenses are often activated by specific interaction between the product of a disease resistance (R) gene in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium fulvum* (Jones et al. (1994)), the tomato Pto gene, which encodes a protein kinase, for resistance to *Pseudomonas syringae* pv. tomato (Martin et al. (1993)), and the Arabidopsis RSSP2 gene for resistance to *Pseudomonas syringae* (Mindrinos et al. (1994)).

(B). A *Bacillus thuringiensis* protein, a derivative thereof or a synthetic polypeptide modeled thereon, such as, a nucleotide sequence of a Bt δ-endotoxin gene (Geiser et al. (1986)). Moreover, DNA molecules encoding δ-endotoxin genes can be purchased from American Type Culture Collection (Rockville, Md.), under ATCC accession numbers. 40098, 67136, 31995 and 31998.

(C) A lectin, such as nucleotide sequences of several *Clivia miniata* mannose-binding lectin genes (Van Damme et al. (1994)).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include a rice cysteine proteinase inhibitor (Abe et al. (1987)), a tobacco proteinase inhibitor I (Huub et al. (1993)), and an α-amylase inhibitor (Sumitani et al. (1993)).

(F) An insect-specific peptide or neuropeptide which, upon expression, disrupts the physiology of the affected pest. Examples of such genes include, an insect diuretic hormone receptor (Regan (1994), an allostatin identified in *Diploptera puntata* (Pratt (1989)), insect-specific, paralytic neurotoxins (U.S. Pat. No. 5,266, 361).

(G) An insect-specific venom produced in nature by a snake, a wasp, etc., such as, a scorpion insectotoxic peptide (Pang (1992)).

(H) An enzyme responsible for a hyperaccumulation of a monoterpene, a sesquiterpene, a steroid, hydroxamic acid, a phenylpropanoid derivative or another non-protein molecule with insecticidal activity.

(I) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al. (1993)) and parsley ubi4-2 polyubiquitin gene (Kawalleck et al. (1993)).

(J) A molecule that stimulates signal transduction. Examples of such molecules include, nucleotide sequences for mung bean calmodulin cDNA clones (Botella et al. (1994)), a nucleotide sequence of a maize calmodulin cDNA clone (Griess et al. (1994)).

(K) A hydrophobic moment peptide. See U.S. Pat. Nos. 5,659,026 and 5,607,914, the latter teaches synthetic antimicrobial peptides that confer disease resistance.

(L) A membrane permease, a channel former or a channel blocker, such as, a cecropin-β lytic peptide analog (Jaynes et al. (1993)) which renders transgenic tobacco plants resistant to *Pseudomonas solanacearum.*

(M) A viral protein or a complex polypeptide derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. (1990).

(N) An insect-specific antibody or an immunotoxin derived therefrom. Thus, an antibody targeted to a critical metabolic function in the insect gut would inactivate an affected enzyme, killing the insect. For example, Taylor et al. (1994) shows enzymatic inactivation in transgenic tobacco via production of single-chain antibody fragments.

(O) A virus-specific antibody. See, for example, Tavladoraki et al. (1993), which shows that transgenic plants expressing recombinant antibody genes are protected from virus attack.

(P) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al. (1992)). The cloning and characterization of a gene which encodes a bean endopolygalacturonase-inhibiting protein is described by Toubart et al. (1992).

(Q) A developmental-arrestive protein produced in nature by a plant, such as the barley ribosome-inactivating gene, have increased resistance to fungal disease (Longemann et al. (1992)).

2. Genes that Confer Resistance or Tolerance to a Herbicide (A) A herbicide that inhibits the growing point or meristem, such as an imidazalinone or a sulfonylurea. Exemplary genes in this category code for mutant ALS (Lee et al. (1988)) and AHAS enzyme (Miki et al. (1990)).

(B) Glyphosate (resistance imparted by mutant EPSP synthase and aroA genes) and other phosphono compounds such as glufosinate (PAT and bar genes), and pyridinoxy or phenoxy proprionic acids and cyclohexones (ACCase inhibitor encoding genes). See, for example, U.S. Pat. No. 4,940,835, which discloses the nucleotide sequence of a form of EPSP synthase which can confer glyphosate resistance. A DNA molecule encoding a mutant aroA gene can be obtained under ATCC accession number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthase genes which confer resistance to herbicides such as L-phosphinothricin. The nucleotide sequence of a phosphinothricin acetyltransferase gene is provided in European application No. 0 242 246. De Greefet al. (1989) describes the production of transgenic plants that express chimeric bar genes coding for phosphinothricin acetyltransferase activity. Exemplary of genes conferring resistance to phenoxy proprionic acids and cyclohexones, such as sethoxydim and haloxyfop, are the Acc1-S1, Acc1-S2 and Acc1-S3 genes described by Marshall et al. (1992).

(C) A herbicide that inhibits photosynthesis, such as a triazine (psbA and GST genes) and a benzonitrile (nitrilase gene). Przibilla et al. (1991) describes the use of plasmids encoding mutant psbA genes to transform Chlamydomonas. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a GST (glutathione S-transferase) is described by Hayes et al. (1992).

3. Genes that Confer Resistance or Tolerance to Environmental Stresses (A) Cold, freezing or frost. This includes genes that code for proteins that protect from freezing and for enzymes that synthesize cryoprotective solutes. Examples of such genes are Arabidopsis COR15a (Artus et al. (1996)) and spinach CAP160 (Kaye et al. (1998)). Also in this category are regulatory genes that control the activity of other cold tolerance genes (Tomashow and Stockinger (1998)).

(B) Drought or water stress. Kasuga et al. (1999) report how stress inducible expression of DREB1A in trangenic plants increases their tolerance of drought stress. Pilin-Smits et al. (1998) report that expression of baterial genes for synthesis of trehalose produces tolerance of water stress in transgenic tobacco.

(C) Salinity or salt stress. Genes that code for proteins that minimize uptake of sodium in the presence of high salt, or cause the plant to sequester sodium in vacuoles, can enable plants to tolerate higher levels of salt in the soil. The wheat HKT1 potassium transporter, described by Rubio et al. (1999), is an example of the former. Apse et al. (1999) describe how an Arabidopsis $Na^+/H^+$ antiporter can act in the latter manner.

(D) Metals. Protection from the toxic effects of metals such as aluminum and cadmium can be accomplished by transgenic expression of genes that prevent uptake of the metal, or that code for chelating agents that bind the metal ions to prevent them from having a toxic effect. Examples of such genes are Arabidopsis ALR104 and ALR108 (Larsen et al. (1998)) and genes for the enzymes involved in phytochelatin synthesis (Schafer et al. (1998)).

4. Genes that Confer or Contribute to a Value-Added Trait (A) Modified fatty acid metabolism, for example, by transforming maize or Brassica with an antisense gene or stearoyl-ACP desaturase to increase stearic acid content of the plant (Knultzon et al. (1992)).

(B) Decreased phytate content
  (1) Introduction of a phytase-encoding gene would enhance breakdown of phytate, adding more free phosphate to the transformed plant, such as the *Aspergillus niger* phytase gene (Van Hartingsveldt et al. (1993)).
  (2) A gene could be introduced that reduces phytate content. In maize, for example, this could be accomplished by cloning and then reintroducing DNA associated with the single allele which is responsible for maize mutants characterized by low levels of phytic acid (Raboy et al. (1990)).

(C) Modified carbohydrate composition effected, for example, by transforming plants with a gene coding for an enzyme that alters the branching pattern of starch. Examples of such enzymes include, *Streptococcus mucus* fructosyltransferase gene (Shiroza et al. (1988)), *Bacillus subtilis* levansucrase gene (Steinmetz et al. (1985)), *Bacillus licheniformis* α-amylase (Pen et al. (1992)), tomato invertase genes (Elliot et al. (1993)), barley amylase gene (Sogaard et al. (1993)), and maize endosperm starch branching enzyme II (Fisher et al. (1993)).

(D) Modified lignin content. The amount or composition of lignin can be altered by increasing or decreasing expression of the biosynthetic enzymes for phenylpropanoid lignin precursors, such as cinnamyl alcohol dehydrogenase (CAD), 4-coumarate:CoA ligase (4CL), and O-methyl transferase (OMT). These and other genes involved in formation of lignin are described in Bloksberg et al. (1998).

4. Selectable Marker Genes (A) Numerous selectable marker genes are available for use in plant transformation including, but not limited to, neomycin phosphotransferase II, hygromycin phosphotransferase, EPSP synthase and dihydropteroate synthase. See, Miki et al. (1993).

Synthesis of genes suitably employed in the present invention can be effected by means of mutually priming long oligonucleotides. See, for example, Ausubel et al. (1990) and Wosnick et al. (1987). Moreover, current techniques which employ the polymerase chain reaction permit the synthesis of genes as large as 6 kilobases in length or longer. See Adang et al. (1993) and Bambot et al. (1993). In addition, genes can readily be synthesized by conventional automated techniques.

EXAMPLES

The present invention is further described in the following examples, which are offered by way of illustration and are not intended to limit the invention in any manner. Standard techniques well known in the art or the techniques specifically described below are utilized.

Example 1

Purification of Nucleic Acids from Sweetgum

Sweetgum flowers from inflorescences were collected from a seed orchard several days prior to anthesis. Female flower clusters were isolated from the bases of the inflorescences before freezing. Male flowers were collected as the intact upper portions of inflorescences, comprising male flower clusters and the main stem of the inflorescences. Expanding vegetative shoots were also collected from the seed orchard trees. Additional leaves, stems (stems plus petioles) and roots were collected from greenhouse-grown seedlings. All tissues were frozen in liquid $N_2$ and stored at −70° C. until use.

Total RNA from the various tissues was prepared using the lithium dodecyl sulfate extraction buffer of Baker et al. (1990) followed by centrifugation through a CsCl gradient. Poly(A)+ RNA was purified from this using Oligotex (QIAGEN). Genomic DNA was purified using the CTAB method (Wagner et al. (1987)).

Example 2

Construction of Libraries and Isolation of DNA Clones

A cDNA library was made from poly(A)+ RNA isolated from female flowers, using Stratagene's LambdaZAP cDNA kit, according to the manufacturer's instructions. This library was plated, transferred to nylon filter circles and probed with radioactively labelled PTAG1, an AGAMOUS homolog from *Populus trichocarpa* (Brunner (1998)). Over twenty clones hybridized to the probe and were purified for further analysis. Preliminary sequencing showed that they were all related to each other, and the two longest clones were completely sequenced.

The genomic DNA library was prepared by partially digesting high molecular weight sweetgum DNA with Sau3AI and filling in the ends with dATP and dGTP to make ends compatible with the modified EMBL13 lambda vector arms provided by Promega. This method prevents genomic DNA fragments from ligating together to make spurious clones, and has a high efficiency. The library was probed with the sweetgum cDNA clone under stringent conditions (hybridization in 5×SSPE, 1% Boehringer Mannheim blocking reagent at 65 C.; final washes in 0.2×SSPE, 0.2% SDS at 65 C.). Three hybridizing clones were purified and shown to overlap by restriction mapping and hybridization analysis. Two of these, λ1-20 and λ1-23, were cleaved with BamHI or EcoRI to produce five fragments that were subcloned into pBluescriptSK for sequencing. The FIGURE shows a map diagramming the region cloned, showing the locations of the exons and showing the origination of the subclones.

Example 3

Sequencing of Clones

All sequencing was based on dideoxynucleotide terminators (Sanger et al. (1977)). Some sequencing to characterize the cDNAs was performed on site using the USB Sequenase 2.0 kit. The majority of the sequencing was performed by the Medical University of South Carolina DNA Sequencing Facility (MUSC), which uses an ABI 377 sequencing apparatus.

In order to bring the vector priming sites adjacent to new sweetgum sequences, deletions of each subclone were made using the Exo III method (Henikoff (1982)). Deletions were chosen for sequencing after determining their sizes by gel electrophoresis. Fluorescent primers were used when deletions were sequenced. For regions within the genomic clones missed by the deletion process, specific sequencing primers were chosen using the Oligo 4.0 software package, and were obtained from Genosys. When MUSC performed sequencing with these primers, fluorescent dideoxynucleotide terminators were used. The gene-specific primers used are set forth in Table 1.

TABLE 1

Primers for Amplifying and Sequencing LSAG

| Primer | Sequence | SEQ ID NO: |
|---|---|---|
| LSAG2-0A | CTTGTGACAACCAAGAGAAGA | 4 |
| LSAG2-0B | TTATTAAGGTTTCAGCATAGACA | 5 |
| LSAG2-5A | TATGGTGTTCCTTTTTCATACTC | 6 |
| LSAG2-5B | AACTTTTTATGGCACAACAAGA | 7 |
| LSAG2-5C | CAATCCCTTCACATTTACTGAGA | 8 |
| LSAG2-5D | TTAGCTCAGGGGAGGTGAAC | 9 |
| LSAG2-5E | CCTTTTTGCAGGTCAATGTTC | 10 |
| LSAG2-5F | GTGGGTATGGAACAGTGACA | 11 |
| LSAG2F | TGCATGGGTAAAAAGAGTACAAC | 12 |
| LSAG2R | AACATCTTGTTCATTTAGTGAAG | 13 |
| LSAG3-7A | GCTATGACAAAAGTGAAGAGG | 14 |
| LSAG3-7B | CTCTGCAGCTATTTGTCTCA | 15 |
| LSAG3-7C | GATTATTAATGGGGTGAATGAG | 16 |
| LSAG3-7D | CCGTTACAGAAGGTGACTTG | 17 |
| LSAG4-3A | CAATGCTATTTTCAGGACTATG | 18 |
| LSAG4-3B | TTCCTCCTAATGTTGCTCTCA | 19 |

TABLE 1-continued

Primers for Amplifying and Sequencing LSAG

| Primer | Sequence | SEQ ID NO: |
|---|---|---|
| LSAG4-3C | CAACCTATCAATCCATTCAAAC | 20 |
| LSAG4-3D | AAAAACCAATGTTTTCTCCTATC | 21 |
| LSAG4-3E | ATTCATGAATGACATCCGTATG | 22 |
| LSAG4-3F | CTTGAAGGTTTTTCGCAGTTCT | 23 |
| LSAG4-3G | CTAGGAGCAGCAACGATAAG | 24 |
| LSAG4-3H | TTAACTGCACAGAAAATACAGG | 25 |
| LSAG4-3I | CAAAAGCTATGTTCAATCAGTC | 26 |
| LSAG4-3J | TTCGCAGGTTTGGGTCATAC | 27 |
| LSAG4-3K | GGTATGATAATGACAAAGTGC | 28 |
| LSAG4-3L | GATGTGGAAACGAGATTGTGT | 29 |
| LSAG5-2A | TCATGCTGCTTTTGAATCCTAA | 30 |
| LSAG5-2B | ACAGATGTCACGGCAGTAATG | 31 |
| LSAG5-2C | AGAGGTATAAGAAGGCATCTG | 32 |
| LSAG5-2D | CATTGGCTTCAGAAACAGATTC | 33 |
| LSAG5-2E | GGTTGGTTTCTTTTGTTCTTAGT | 34 |
| LSAG5-2F | GAATAACAGTTTTGAGGGTCTT | 35 |
| LSAGS-2G | TTCCATTGCACTATCTAAACATC | 36 |

Example 4

Hybridization Analysis of Genomic DNA

To determine the number of times that LSAG or closely related sequences were present in the genome and to verify that the structure of the cloned DNA accurately reflected that of the original genomic DNA, several restriction digests were performed on clone λ1-23 and sweetgum DNA. The enzymes were chosen to produce fragments that were fully contained in λ1-23, with both ends in the sequenced region. It was assumed that the sweetgum haploid genome contains approximately 1.0 pg of DNA, and in order to make the signals from the two DNAs have the same intensity, 50 pg of λ1-23 was loaded next to 10 g of sweetgum DNA. The DNA was separated by electrophoresis on a 0.7% agarose gel and transferred to a nylon membrane by standard methods (Sambrook et al. (1989)). The hybridization pattern showed that there is a single copy of the gene in sweetgum, and that the cloned DNA accurately represents the structure of the genomic DNA.

Example 5

LSAG Gene

Two near-full-length cDNA clones and two overlapping genomic clones corresponding to the sweetgum homolog of the AGAMOUS gene have been sequenced. The cDNA for the sweetgum LSAG gene is shown in SEQ ID NO:1 with the corresponding amino acid sequence shown in SEQ ID NO:2. The sweetgum LSAG gene is approximately 17 kilobases (kb) long, with seven exons encoding the final transcript. The genomic sequence with the exons and introns is set forth in SEQ ID NO:3. The sequences from SEQ ID NO:3 corresponding to the exons and introns are set forth in Table 2. The second intron, which contains regulatory information necessary for keeping expression specific to flowers, is over 8 kb long.

TABLE 2

Exons and Introns of the LSAG Gene

| Exon/Intron | 5' Nucleotide | 3' Nucleotide |
|---|---|---|
| Exon 1 | <3710 | 3946 |
| Intron 1 | 3947 | 4245 |
| Exon 2 | 4246 | 4481 |
| Intron 2 | 4482 | 12967 |
| Exon 3 | 12968 | 13049 |
| Intron 3 | 13050 | 13606 |
| Exon 4 | 13607 | 13668 |
| Intron 4 | 13669 | 13747 |
| Exon 5 | 13748 | 13847 |
| Intron 5 | 13848 | 13993 |
| Exon 6 | 13994 | 14035 |
| Intron 6 | 14036 | 14527 |
| Exon 7 | 14528 | 14839 |
| Intron 7 | 14840 | 15722 |
| Exon 8 | 15723 | 16009 |

The LSAG gene was searched for the CCANTG motif that has recently been reported to contribute to expression in flowers by serving as a binding site for LEAFY (Busch et al. (1999)). Over 30 such sites were found as shown in Table 3. This gene sequence is one of the first such pieces of data available for the species. Analysis of the DNA sequences reveals that the DNA is A/T-rich, and that there are several types of simple sequence repeats, also shown in Table 3. These repeats may prove useful for mapping the sweetgum genome.

TABLE 3

Frequencies and Locations of Simple Sequence Repeats (SSRs) and CCANTG Motifs in the LSAG Gene

| Sequence | Number of Occurrences | Position (Value of n) | | |
|---|---|---|---|---|
| (A)n | 5 | 586 (24) | 3377 (17) | 5490 (10) |
|  |  | 8501 (21) | 17395 (14) |  |
| (C)n | 1 |  | 558 (22) |  |
| (T)n | 7 | 5324 (12) | 6250 (11) | 9742 (10) |
|  |  | 9866 (12) | 10509 (10) | 10897 (13) |
|  |  | 13967 (12) |  |  |
| (AG)n | 4 | 265 (24*) | 2748 (8*) | 3714 (15) |
|  |  | 6083 (6) |  |  |
| (AT)n | 5 | 10024 (12) | 10585 (11) | 11876 (25*) |
|  |  | 12070 (12) | 12857 (8) |  |
| (CT)n | 5 | 3525 (18*) | 4999 (24*) | 5811 (21*) |
|  |  | 11842 (12) | 14572 (14) |  |
| (GT)n | 1 |  | 10894 (15*) |  |
| (CTTT)n | 1 |  | 413 (4) |  |
| (GAAA)n | 1 |  | 8528 (8*) |  |
| CCANTG | 31 | 2023 | 2304 | 2915 |
|  |  | 3567 | 4513 | 4944 |
|  |  | 5047 | 5692 | 6122 |
|  |  | 6183 | 6388 | 6452 |
|  |  | 6491 | 7154 | 8007 |
|  |  | 8963 | 9785 | 11229 |
|  |  | 11624 | 13039 | 13053 |
|  |  | 14908 | 14938 | 15151 |
|  |  | 15643 | 15851 | 16433 |
|  |  | 16494 | 17309 | 17346 |
|  |  |  | 17640 |  |

*Imperfect repeat

Example 6

Isolation of LSAG Promoter

Although the promoter region of Arabidopsis AGAMOUS is not sufficient to direct flower-specific expression of a transgene (Sieburth and Meyerowitz (1997)), the promoter of a homolog from a divergent species such a sweetgum may possess this ability. An approximately 2 kb region of the LSAG gene upstream of the cDNA sequence contains four CCANTG motifs that are possible binding sites for LEAFY, which stimulates AGAMOUS expression. It is expected that the same mechanism functions in sweetgum. The sequence data provided here enable PCR primers to be synthesized for amplification of the isolated LSAG promoter. It is not necessary to know the exact location of the transcriptional start site. The first (forward) primer should preferably be located between positions 1 and 2000 of SEQ ID NO:3 and the second (reverse) primer should be located downstream of the first base known to be in a transcript (position 3710 of SEQ ID NO:3). The reverse primer should not be chosen so that a partial fragment of the first intron (positions 3947–4245 of SEQ ID NO:3) is included in the amplified fragment. It is acceptable for the reverse primer to be complementary to the sequences at and flanking the presumed start of translation (position of SEQ ID NO:3), which would mean that the first intron of LSAG would be contained intact within the amplified fragment.

The specificity of transcription provided by the promoter fragment can be determined by operably linking it to the β-glucuronidase (GUS) reporter gene (Jefferson et al. (1987)) in an appropriate vector and transforming tobacco, Arabidopsis, sweetgum, or other plant species. Visualization of GUS enzyme activity will demonstrate the function of the amplified fragment. If any blue pigment is seen, it shows that the amplified sequence can direct transcription and is a functional promoter. If the pigment is limited to only developing flower buds, preferably the stamens, pistils, and their primordia, the promoter fragment contains regulatory sequences for flower-specific expression.

Example 7

Isolation of LSAG Regulatory Sequence

If the promoter of LSAG proves unable to direct flower-specific expression, it is most likely that the necessary information will be found in the second intron, corresponding to where it resides in Arabidopsis AGAMOUS. The large 8.5 kb second intron of LSAG contains 15 CCANTG sequences that could possibly be involved in flower-specific expression (Table 2). To identify which of them is/are functional regulatory sequences (enhancers), fragments of the second intron must be combined with a promoter that is not able to direct flower-specific expression on its own. In the case of the AGAMOUS gene, the intron fragments were linked with a minimal promoter from the cauliflower mosaic virus 35S transcript, with the GUS reporter gene used to visualize the expression pattern (Busch et al. (1999)). Using the data from SEQ ID NO:3 positions 4482–12967, PCR primers can be designed to amplify subfragments of the intron. These fragments can then be linked in front of the minimal promoter::GUS construct, transformed into a plant, and tested for the expression pattern of GUS activity, similar to the process described in the previous section. By choosing overlapping fragments for analysis, the location of enhancer elements can be narrowed to smaller and smaller regions.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Abe et al. (1987). *J. Biol. Chem.* 262:16793.
Adang et al. (1993). *Plant Molec. Biol.* 21:1131.

Anand, R. (1992). *Techniques for the Analysis of Complex Genomes*, (Academic Press).
Altschul, S. F. et al. (1990). *J. Mol. Biol.* 215:403.
Altschul, S. F. et al. (1997). *Nuc. Acids Res.* 25:3389–3402.
Apse, M. P. et al. (1999). *Science* 285:1256–1258.
Artus, N. N. et al. (1996). *Proc. Natl. Acad. Sci USA* 93:13404–13409.
Ausubel et al. (1990). *Current Protocols in Molecular Biology*, Wiley Interscience, pp. 8.2.8–8.2.13.
Ausubel, F. M. et al. (1992). *Current Protocols in Molecular Biology*, (John Wiley & Sons, New York, N.Y.).
Baker, S. S. et al. (1990). *Bio/Techniques* 9:268–272.
Bambot et al. (1993). *PCR Methods and Applications* 2:266.
Beachy et al. (1990). *Ann. Rev. PhytopathoL* 28:451.
Beaucage, S. L. and Caruthers, M. H. (1981). *Tetra. Letts.* 22:1859–1862.
Beetham P. R. (1999). *Proc. Natl. Acad. Sci USA* 96:8774–8778.
Binding, H. (1985). Regeneration of Plants, *Plant Protoplasts* (CRC Press), pp. 21–73.
Biocomputing: Informatics and Genome Projects, Smith, D. W., ed., Academic Press, Press, NY (1993).
Bloksberg, L. N. et al. (1998). U.S. Pat. No. 5,850,020.
Botella et al. (1994). *Plant Molec. Biol.* 24:757.
Bridges et al. (1990). PCT International Publication No. WO 90/08829.
Brunner, A. (1998). Structure and expression of two *Populus trichocarpa* homologs of the floral homeotic gene AGAMOUS. Ph.D. Dissertation, Department of Forest Science, Oregon State University, Corvallis.
Busch, M. A. et al. (1999). *Science* 285:585–588.
Carillo, H. and Lipman, D. (1988). *SIAM J. Applied Math.* 48:1073.
Chaubet et al. (1987). *Devel. Genet.* 8:461–473.
Compton, J (1991). *Nature* 350:91–92.
*Computational Molecular Biology*, Lesk, A. M., ed., Oxford Univ. Press, NY (1988).
*Computer Analysis of Sequence Data*, Part I, Griffm, A. M., and Griffin, H. G., eds., Humana Press, NJ (1994).
Davey, M. R. (1983). Recent Developments in the Culture and Regeneration of Plant Protoplasts, *Protoplasts* (1983) *Lecture Proceedings*, pp. 12–29 (Birkhauer Basil).
DeGreef, W. et al. (1997). Plants with genetic female sterility, U.S. Pat. No. 5,633,441.
DeGreef et al. (1989). *Bio/Technology* 7:61.
Deutscher, M (1990). *Meth. Enzymology* 182:83–89 (Academic Press, San Diego, Calif.).
Devereux, J et al. (1984). *Nucl. Acids Res.* 12(1):387.
Elliot et al. (1993). *Plant Molec. Biol.* 21:515.
*Enhancers and Eukaryotic Gene Expression*, Cold Spring Harbor Laboratory, Cold Spring Harbor, N.Y. (1983).
Evans et al. (1983). Protoplasts Isolation and Culture, *Handbook of Plant Cell Cultures* 1: 124–176 (MacMillan Publishing Co., NY).
Fahy, E et al. (1991). *PCR Methods Appl.* 1:25–33.
Fiers, W et al. (1978). *Nature* 273:113–120.
Fisher et al. (1993). *Plant Physiol.* 102:1045.
Fraley et al. (1983). *Proc. Nat. Acad. Sci. USA* 80:4803.
Fromm et al. (1985). *Proc. Nat. Acad. Sci. USA* 82:5824.
Geiser et al. (1986). *Gene* 48:109.
Gelvin, S. et al. (eds) (1990). *Plant Molecular Biology: Manual*, Kluwer Academic Press, Dordrecht, Netherlands
Glover, D (1985). *DNA Cloning*, I and II (Oxford Press).
Griess et al. (1994). *Plant Physiol.* 104:1467.
*Guide to Huge Computers*, Martin J. Bishop, ed., Academic Press, San Diego, Calif. (1994).
Guilley et al. (1982). *Cell* 30:763–773 (1982).
Guthrie, G and Fink, G. R. (1991). *Guide to Yeast Genetics and Molecular Biology* (Academic Press).
Hamilton et al. (1992). *Plant Molecular Biology* 18:211–218.
Hammock et al. (1990). *Nature* 344:458.
Hayes et al. (1992). *Biochem. J.* 285:173.
Henikoff, S. (1984). *Gene* 28: 351–359.
Hohn et al. (1982). *Molecular Biology of Plant Tumors* (Academic Press, NY), pp. 549–560.
Horsch et al. (1984). *Science* 233:496–498.
Huub et al. (1993). *Plant Molec. Biol.* 21:985.
Innis, M. A. et al. (1990). *PCR Protocols: A Guide to Methods and Applications* (Academic Press, San Diego, Calif.).
Jakoby, W. B. and Pastan, I. H. (eds.) (1979). *Cell Culture, Methods in Enzymology* Vol. 58 (Academic Press, Inc., Harcourt Brace Jovanovich (NY)).
Jaynes et al. (1993). *Plant Sci.* 89:43.
Jefferson, R. A. et al. (1987). *EMBO J.* 6:3901–3907.
Jones et al. (1994). *Science* 266:789.
Kanehisa, M (1984). *Nucl. Acids Res.* 12:203–213.
Kasuga M. et al. (1999). *Nature Biotech.* 17:287–291.
Kawalleck et al. (1993). *Plant Molec. Biol.* 21:673.
Kaye, C et al. (1998). *Plant Physiol.* 116:1367–1377.
Kempin, S. A. et al. (1997). *Nature* 389:802–803.
Klee et al. (1987). *Ann. Review of Plant Physiology* 38:467–486.
Klein et al. (1987). *Nature* 327:70–73.
Knultzon et al. (1992). *Proc. Nat. Acad. Sci. USA* 89:2624.
Kramer et al. (1993). *Insect Molec. Biol.* 23:691.
Kubo, T et al. (1988). *FEBS Lett.* 241:119.
Kyte, J and Doolittle, R. F. (1982). *J. Mol. Biol.* 157:105–132.
Lamb et al. (1992). *Bio/Technology* 10:1436.
Larsen, P. B. et al. (1998). *Plant Physiol.* 117: 9–18.
Lee et al. (1988). *EMBO J.* 7:1241.
Leutwiler et al. (1986). *Nucl. Acids Res.* 14:4051–4064.
Levy, Y. and Dean, C. (1998). *Plant Cell* 10:1973–1989.
Livak et al. (1978). *Proc. Nat. Acad. Sci. USA* 75:5613–5617.
Longemann et al. (1992). *Bio/Technology* 10:3305.
Maas, C. et al. (1997). *Mol. Breeding* 3:15–28.
Maniatis, T et al. (1982). *Molecular Cloning:A Laboratory Manual* (Cold Spring Harbor Laboratory, Cold Spring Harbor, N.Y.).
Mariani, C et al. (1989). PCT International Publication Number WO 89/10396.
Mariani, C et al. (1998). Plants with modified flowers,. U.S. Pat. No. 5,723,763.
Marshall et al. (1992). *Theor. Appl. Genet.* 83:435.
Martinet al. (1993). *Science* 262:1432.
Matteucci, M. D. and Caruthers, M. H. (1981). *J. Am. Chem. Soc.* 103:3185.
Metzger, D et al. (1988). *Nature* 334:31–36.
Meyerowitz, E. M. et al. (1998). U.S. Pat. No. 5,744,693.
Miki et al. (1990). *Theor. Appl. Genet.* 80:449.
Miki et al. (1993). "Procedures for Introducing Foreign DNA into Plants," in *Methods in Plant Molecular Biology and Biotechnology*, Glick et al. (eds.), CRC Press, pp. 67–88.
Mindrinos et al. (1994). *Cell* 78:1089.
Mizukami, Y. et al. (1996). *Plant Cell* 8: 831–845.
Mol, J. M. N. et al. (1994). Post-transcriptional inhibition of gene expression: sense and antisense genes. In: J. Paszkowski (Ed.). *Homologous Recombination and Gene Silencing in Plants*. Kluwer Academic Publishers. Dordrecht, Netherlands. pp. 309–334.

Monsour et al. (1988). *Nature* 336:348–352.
Nasrallah, M. E. et al (1994). PCT International Publication Number WO 94/25613.
Norris, S. R. et al. (1993). *Plant Mol. Biol.* 21:895–906.
Odell et al. (1985). *Nature* 313:810–812.
Oliver, M. J. et al. (1998). U.S. Pat. No. 5,723,765.
Pang et al. (1992). *Gene* 116:165.
Paskowski et al. (1984). *EMBO J.* 3:2717–2722.
Pen et al. (1992). *Bio/Technology* 10:292.
Pilon-Smits E. A. H. et al. (1998). *J. Plant Physiol.* 152:525–532.
Przibilla et al. (1991). *Plant Cell* 3:169.
Raboy et al. (1990). *Maydica* 35:383.
Regan (1994). *J. Biol. Chem.* 269:9.
Rethmeier, N. et al. (1996). *Plant J.* 12:895–899.
Sambrook, J. et al. (1989). *Molecular Cloning: A Laboratory Manual,* 2nd Ed. (Cold Spring Harbor Laboratory, Cold Spring Harbor, N.Y.).
Sanders et al. (1987). *Nuc. Acids Res.* 15:1543–1558.
Sanger, F. et al. (1977). *Proc. Nat. Acad. Sci. USA* 74:5463–5467.
Schafer, H. J. et al. (1998). *Plant Mol. Biol.* 37:87–97.
Scharf, S. J. et al. (1986). *Science* 233:1076–1078.
Schmitt, D. M. (1964). Self-sterility in sweetgum. Ph.D. Thesis Dissertation, North Carolina State University.
Scopes, R (1982). *Protein Purification: Principles and Practice,* (Springer-Verlag, NY).
*Sequence Analysis in Molecular Biology,* von Heinje, G., Academic Press (1987).
*Sequence Analysis Primer,* Gribskov, M. and Devereux, J., eds., M Stockton Press, NY (1991)
*Sequence Analysis Software Package of the Genetics Computer Group.* Univ. of Wisconsin Biotechnology Center, Madison, Wis.
Shiroza et al. (1988). *J. Bacteriol.* 170:810.
Sieburth, L. E. and Meyerowitz, E. M. (1997). *Plant Cell* 9:355–365.
Silflow et al. (1987). *Devel. Genet.* 8:435–460.
Søgaard et al. (1993). *J. Biol. Chem.* 268:22480.
Spargo, C. A. et al. (1996). *Mol. Cell. Probes* 10:247–256.
Springer, P. S. et al. (1995). *Science* 268:877–880.
Steinmetz et al. (1985). *Mol. Gen. Genet.* 200:220.
Strauss, S H and Meilan, R (1998). Tree Genetic Engineering Research Cooperative 1998 Annual Report.
Sumitani et al. (1993). *Biosci. Biotech. Biochem.* 57:1243.
Takahashi et al. (1989). *Mol. Gen. Genet.* 219:365–372.
Taylor, L. P. and Jorgensen, R. A. (1992). *J. Hered.* 83:11–17.
Taylor et al. (1994). Abstract #497, Seventh Int'l. Symposium on Molecular Plant-Microbe Interactions.
Tavladoraki et al. (1993). *Nature* 266:469.
Teasdale, R. D. (1992). PCT International Publication Number WO 92/05257.
Tomashow, M. F. and Stockinger E J. (1998). PCT International Publication Number WO 98/09521.
Toubart et al. (1992). *Plant J.* 2:367.
Tuttle, A. B. and Crossland, L. D. (1995). U.S. Pat. No. 5,477,002.
Vain, P. et al. (1993). *Plant Cell, Tissue and Organ Culture* 33:237–246.
Van Damme et al. (1994). *Plant Molec. Biol.* 24:825.
Van Hartingsveldt et al. (1993). *Gene* 127:87.
Vorst et al. (1990). *Plant Mol. Biol.* 14:491–499.
Wagner D B et al. (1987). *Proc. Natl. Acad. Sci. USA* 84:2097–2100.
Walker, G T et al. (1992). *Nucl. Acids Res.* 20:1691–1696.
Weissbach, A. and Weissbach, H. (eds) 1986. *Methods in Enzymology,* Volume 118, Academic Press, Inc., Orlando, Fla.
Wetmur, J G and Davidson, N (1968). *J. Mol. Biol.* 31:349–370.
Wosnick et al. (1987). *Gene* 60:115.
Wu, D Y and Wallace, R B (1989). *Genomics* 4:560–569.
Wu and Grossman (1987). *Methods and Enzymology,* Vol. 153, "Recombinant DNA Part D". Academic Press, NY.
Zaitlin, M. et al. (eds) (1985). *Biotechnology in Plant Science,* Academic Press, Inc., Orlando, Fla.
Patents and Patent Applications
Hitzeman et al., EP 73,675A.
PCT International Publication Number WO 92/05257.
PCT published application No. WO 93/02197.
PCT International Publication Number WO 98/09521.
European published application No. 0 242 246.
European published application No. 0 333 033.
U.S. Pat. No. 4,554,101.
U.S. Pat. No. 4,683,195.
U.S. Pat. No. 4,683,202.
U.S. Pat. No. 5,266,361.
U.S. Pat. No. 5,270,184.
U.S. Pat. No. 5,409,818.
U.S. Pat. No. 5,436,146.
U.S. Pat. No. 5,455,166.
U.S. Pat. No. 5,633,441.
U.S. Pat. No. 5,691,198.
U.S. Pat. No. 5,735,500.
U.S. Pat. No. 5,747,469.
U.S. Pat. No. 4,769.061.
U.S. Pat. No. 4,810,648.
U.S. Pat. No. 4,940,835.
U.S. Pat. No. 4,975,374.
U.S. Pat. No. 5,106,739.
U.S. Pat. No. 5,268,526.
U.S. Pat. No. 5,290.294.
U.S. Pat. No. 5,322,938.
U.S. Pat. No. 5,607,914.
U.S. Pat. No. 5,659,026.
U.S. Pat. No. 5,710,267.
U.S. Pat. No. 5,808,034.
U.S. Pat. No. 5,850,020.

What is claimed is:

1. An isolated DNA comprising a nucleic acid or its complement, said nucleic acid comprises a nucleotide sequence coding for sweetgum LSAG comprising an amino acid sequence set forth in SEQ ID NO:2.

2. The isolated DNA of claim 1, wherein said nucleic acid comprises (a) a nucleotide sequence set forth in SEQ ID NO:1 or its complement or (b) a nucleotide sequence comprising nucleotides 331–1008 set forth in SEQ ID NO:1 or its complement.

3. A DNA molecule comprising a first nucleic acid comprising a heterologous promoter operably linked to the isolated DNA of claim 1 or a fragment thereof which is capable of decreasing endogenous LSAG expression in sweetgum by an antisense mechanism or a sense suppression mechanism.

4. The DNA molecule of claim 3, wherein said endogenous LSAG expression is decreased by an antisense mechaniism.

5. The DNA molecule of claim 3, wherein said endogenous LSAG expression is decreased by a sense suppression mechanism.

6. A DNA molecule comprising a first nucleic acid comprising a heterologous promoter operably linked to the isolated DNA of claim 2 or a fragment thereof which is capable of decreasing endogenous LSAG expression in sweetgum by an antisense mechanism or a sense suppression mechanism.

7. The DNA molecule of claim 6, wherein said endogenous LSAG expression is decreased by an antisense mechanism.

8. The DNA molecule of claim 6, wherein said endogenous LSAG expression is decreased by a sense suppression mechanism.

9. A vector comprising the DNA molecule of claim 3.

10. A vector comprising the DNA molecule of claim 6.

11. A transformed sweetgum cell comprising the isolated DNA of claim 1 or a fragment thereof which is capable of decreasing endogenous LSAG expression in sweetgum by an antisense mechanism or a sense suppression mechanism.

12. A transformed sweetgum cell comprising the isolated DNA of claim 2 or a fragment thereof which is capable of decreasing endogenous LSAG expression in sweetgum by an antisense mechanism or a sense suppression mechanism.

13. A transformed sweetgum cell comprising the DNA molecule of claim 3.

14. A transformed sweetgum cell comprising the DNA molecule of claim 6.

15. A transformed sweetgum comprising the isolated DNA of claim 1 or a fragment thereof which is capable of decreasing endogenous LSAG expression in sweetgum.

16. A transformed sweetgum comprising the isolated DNA of claim 2 or a fragment thereof which is capable of decreasing endogenous LSAG expression in sweetgum.

17. A transformed sweetgum comprising the DNA molecule of claim 3.

18. A transformed sweetgum comprising the DNA molecule of claim 6.

19. A method for producing transgenic sweetgum having decreased endogenous LSAG expression comprising transforming sweetgum cells with the DNA molecule of claim 3, selecting transformed sweetgum cells comprising said DNA molecule and regenerating transgenic sweetgum having decreased endogenous LSAG expression from said transformed sweetgum cells.

20. A method for producing transgenic sweetgum having decreased endogenous LSAG expression comprising transforming sweetgum cells with the DNA molecule of claim 6, selecting transformed sweetgum cells comprising said DNA molecule and regenerating transgenic sweetgum having decreased endogenous LSAG expression from said transformed sweetgum cells.

* * * * *

UNITED STATES PATENT AND TRADEMARK OFFICE
CERTIFICATE OF CORRECTION

PATENT NO. : 6,444,877 B1
DATED : September 3, 2002
INVENTOR(S) : William Horn Rottmann It is certified that error appears in the above-identified patent and that said Letters Patent is hereby corrected as shown below:

Title page,
Item [56], References Cited, OTHER PUBLICATIONS, after "Sieburth, L.E." insert therefor -- et al. --.

Column 18,
Line 34, delete "Bamase" and substitute therefor -- Barnase --.

Column 22,
Line 61, delete "Greefet" and substitute therefor -- Greef et --.

Column 30,
Line 51, delete "Martinet" and substitute therefor -- Martin et --.

Column 59,
Lines 54-55, delete "mechaniism" and substitute therefor -- mechanism --.

Signed and Sealed this

Seventeenth Day of December, 2002

JAMES E. ROGAN
*Director of the United States Patent and Trademark Office*

SEQUENCE LISTING

<160> NUMBER OF SEQ ID NOS: 36

<210> SEQ ID NO 1
<211> LENGTH: 1297
<212> TYPE: DNA
<213> ORGANISM: Liquidambar styraciflua

```
<220> FEATURE:
<221> NAME/KEY: CDS
<222> LOCATION: (331)..(1008)

<400> SEQUENCE: 1
gaattcggca cgagacaaaa tatatagatt cacagagaga gagagataga gagagagaga      60
gagagagaga gagaggaata tatagtatat agaaaattaa gttggaagtg cttgataatg     120
gatgaagggt catttctaac tttataaata cccatctctg agaactacgt ccttccattt     180
tctgcttctc tctgtccaga tttgagagaa accaaggcag aaacctttgt ttccgtcctt     240
aattatctcc ttcccggccc tttgtttctt caccagcttt caaccacggc tttcgtaaac     300
caatcgaggg aggtatctcc ccagagaaaa atg ggt agg gga aag atc gag atc     354
                                   Met Gly Arg Gly Lys Ile Glu Ile
                                    1               5 aag cgg atc gag aac acg aca aac cgc caa gtc acc ttc tgt aaa cgg     402
Lys Arg Ile Glu Asn Thr Thr Asn Arg Gln Val Thr Phe Cys Lys Arg
         10                  15                  20 cgc aac ggc tta ctc aag aag gcc tat gaa tta tct gtt ctc tgt gat     450
Arg Asn Gly Leu Leu Lys Lys Ala Tyr Glu Leu Ser Val Leu Cys Asp
 25                  30                  35                  40 gcc gag gta gcc ctt atc gtc ttc tct acc cgt ggc cgc ctt tac gag     498
Ala Glu Val Ala Leu Ile Val Phe Ser Thr Arg Gly Arg Leu Tyr Glu
                 45                  50                  55 tat gcc aac aac agt gtt aaa gca aca att gag agg tat aag aag gca     546
Tyr Ala Asn Asn Ser Val Lys Ala Thr Ile Glu Arg Tyr Lys Lys Ala
             60                  65                  70 tct gtg gat tcc tcc aat act gga tct gtt tct gaa gcc aat gct cag     594
Ser Val Asp Ser Ser Asn Thr Gly Ser Val Ser Glu Ala Asn Ala Gln
         75                  80                  85 ttc tac cag caa gaa gct ggc aaa ctg cgt aac caa atc agg aat atg     642
Phe Tyr Gln Gln Glu Ala Gly Lys Leu Arg Asn Gln Ile Arg Asn Met
 90                  95                 100 cag aat aca aac agg act atg ctg ggt gag tct ttg ggc tct ctg agt     690
Gln Asn Thr Asn Arg Thr Met Leu Gly Glu Ser Leu Gly Ser Leu Ser
105                 110                 115                 120 ccc aaa gaa ctc aag ggt ctg gag act aaa tta gag aaa ggc att agc     738
Pro Lys Glu Leu Lys Gly Leu Glu Thr Lys Leu Glu Lys Gly Ile Ser
                125                 130                 135 aaa ata agg tcc aaa aag aat gag cta ctg ttt tcc gaa att gaa tac     786
Lys Ile Arg Ser Lys Lys Asn Glu Leu Leu Phe Ser Glu Ile Glu Tyr
            140                 145                 150 atg caa aag agg gaa atc gac ttg cac aat gat aac cag tat ctc cga     834
Met Gln Lys Arg Glu Ile Asp Leu His Asn Asp Asn Gln Tyr Leu Arg
        155                 160                 165 gca aaa ata gct gaa cac gag aga gct caa cag caa atg aac ttg atg     882
Ala Lys Ile Ala Glu His Glu Arg Ala Gln Gln Gln Met Asn Leu Met
    170                 175                 180 cca ggt gga tca aac tat gag gtc ttg cca tca cag cca ttt gac tct     930
Pro Gly Gly Ser Asn Tyr Glu Val Leu Pro Ser Gln Pro Phe Asp Ser
185                 190                 195                 200 cgg aac ttt ttc caa gta aat gca ttg caa ccc aat cat cat tac tct     978
Arg Asn Phe Phe Gln Val Asn Ala Leu Gln Pro Asn His His Tyr Ser
                205                 210                 215 cgc caa gat caa atg gcc ctt caa tta gtt taatgggcct gaaggagagc      1028
Arg Gln Asp Gln Met Ala Leu Gln Leu Val
            220                 225 taatatctac tttgtttata ttctgtggaa ggaatctact attctaccag attaagctat    1088
gtgtaagttg agataaaagc agtgaccaaa ctgtattcca gtggagggct ttagtattct    1148
```

```
ctgatgggtt gttagcttct tagaagatca taagactcct aacaatgtta ttagctagtg    1208
aaagacatct tttctgtatg ttttatgcaa gcactaccat gctataacag atactactta    1268
tgtatttctt atgctttgtg tgatttaaa                                      1297

<210> SEQ ID NO 2
<211> LENGTH: 226
<212> TYPE: PRT
<213> ORGANISM: Liquidambar styraciflua

<400> SEQUENCE: 2

Met Gly Arg Gly Lys Ile Glu Ile Lys Arg Ile Glu Asn Thr Thr Asn
 1               5                  10                  15

Arg Gln Val Thr Phe Cys Lys Arg Arg Asn Gly Leu Leu Lys Lys Ala
            20                  25                  30

Tyr Glu Leu Ser Val Leu Cys Asp Ala Glu Val Ala Leu Ile Val Phe
        35                  40                  45

Ser Thr Arg Gly Arg Leu Tyr Glu Tyr Ala Asn Asn Ser Val Lys Ala
    50                  55                  60

Thr Ile Glu Arg Tyr Lys Lys Ala Ser Val Asp Ser Ser Asn Thr Gly
65                  70                  75                  80

Ser Val Ser Glu Ala Asn Ala Gln Phe Tyr Gln Gln Glu Ala Gly Lys
                85                  90                  95

Leu Arg Asn Gln Ile Arg Asn Met Gln Asn Thr Asn Arg Thr Met Leu
           100                 105                 110

Gly Glu Ser Leu Gly Ser Leu Ser Pro Lys Glu Leu Lys Gly Leu Glu
        115                 120                 125

Thr Lys Leu Glu Lys Gly Ile Ser Lys Ile Arg Ser Lys Lys Asn Glu
    130                 135                 140

Leu Leu Phe Ser Glu Ile Glu Tyr Met Gln Lys Arg Glu Ile Asp Leu
145                 150                 155                 160

His Asn Asp Asn Gln Tyr Leu Arg Ala Lys Ile Ala Glu His Glu Arg
                165                 170                 175

Ala Gln Gln Gln Met Asn Leu Met Pro Gly Gly Ser Asn Tyr Glu Val
            180                 185                 190

Leu Pro Ser Gln Pro Phe Asp Ser Arg Asn Phe Phe Gln Val Asn Ala
        195                 200                 205

Leu Gln Pro Asn His His Tyr Ser Arg Gln Asp Gln Met Ala Leu Gln
    210                 215                 220

Leu Val
225

<210> SEQ ID NO 3
<211> LENGTH: 17656
<212> TYPE: DNA
<213> ORGANISM: Liquidambar styraciflua

<400> SEQUENCE: 3
ggatcccggg aattctcgat cttatatcaa ggtaatatca atagagaaaa tcatgtactt      60 gaaaaaaga aactattaat tttccatttt ctgctaaaca agtcaaacct atttttgat     120 tctgtgattg tttgaaatgg ttcttgttaa acaaccaaac aaaacctaac aacaaggtta    180
aactaataat gcatctaatc ttagagcata taatttctat tagggtactg actgattttg    240
aattattcca tgcgttgtgt catggagaga gagagagaga gagagagaga gagagagaga    300
aagagagaga gagggcagga tgttttcgct ctttattttg gcttttattt tcattaaaat    360
```

-continued

```
gccatatata ttaagaaaag cttatggtgt tcctttttca tactctctaa tactttcttt    420
ctttctttta tttattttgt taattatatg attagttttt aattcagata aataatctca    480
gtaaatgtga agggattctt tgatttatag ggttttttaac aattttattg tgctaaaaat   540
taaccaccaa cacctctccc cctccccccc cccccccccc ccccaaaaa aaaaaaaaa     600 aaaaaaaaac tttttctatg tgctgaagta agagtgtggt attagtttcc ctcaatgtgg   660
tcctcataga agatatgatg aagattttct tgttgtgccc ataaaagtt ttgacctcta    720 agaactctgg taattaccat gaccatttta ttttagaaat aacctcattt agacgtgaca   780
ccccaagtag aaggtgcatg tgaatgtctt gagaaagttt atgcatatga atacaaagaa   840
agaaagataa tatgtatctt gaactcaatc aaaacattga tgagatcata aattttttgga  900 agataactga acagtgtcat caaagtacca tataaagcac attgtatcat caaacatttt   960 ttgggggggtc tctcatttaa ttattaaatc tagccaatac aagaatgctg aggtggttga  1020
gtggaaagaa taggaaaaat aactttgtat tagcgcaact aaaagactcc caagaaatta  1080 aaataaaaa ataaaaaaaa ataaaaaaag aaaagaaaaa aaaagacccc caggaaggcc   1140
caattaattg acgaggaaga ttggaacctt gtattggatc gacccaggga cagtgctagc  1200
acataactag gggggcagcc gcctcccctc attttttccc aaaaatgtct tataccttaa  1260
tttatttatt tattattttt caaaaaaatt tcagatttat ctcgcctaat tgttttaata  1320
tccttttttt tcttttccca cccctctcat ttttttatttt tcttgccta taaaatcccc  1380 aatccccaat cctctctctc aatctctcat tttatacaac gctttcaaaa aatgagacct  1440
tgtcaaggat aattgtaaat gtattaaatt gaaaatataat ttatcaatag attataaatt  1500
tttgtaattt tgtttacatc aaaatcacaa gataaaagaa aaaattttaa gctatactaa  1560
caactaacca aagttcacct cccctgagct aaattcctag ctccgtcctt ggatcgatcc  1620
tagccaccat caaattggtc ctatttctta agaagtttca taggattcaa cagggcgaga  1680
tgagttgcag ttatcatttg tatacatatc ttatgtgtaa aattcattaa agttttttcaa  1740 cttgtacaga attatgaaaa ggcaaaaact tcagactctt gattaaaaaa ttgcatgaac  1800
attgacctgc aaaaggcag agcatgatct gtgttgcaaa tgccaaataa ttcaaaaaag  1860
gcatttctga ttgatattgt actagtactc caaactctag taactttacc cctttttat   1920 ctagtaaatg gtcaatgtat agtttaccca gctttctaga agcagacacg agagccaagg  1980
cctgtgtatt aagtttagtt tgtcaaagaa atatgtagtg ctccattgaa cataggatgg  2040
gtacctagca catatattgt gatagcgaat caaccattta tttgtctttc ttcgaattat  2100
gcatcaaaga agcgaaccat caacaaacac tatggactaa aaagcaaatg gggtatttgt  2160
agtattggga acactacatt ttctttgcga aagaaaagac ctatcgtggc tacgttttat  2220
atgaattcca aggtgggtat ggaacagtga catatgctga tctacaacaa caattgtagt  2280
ggcacaaagc gacgtggaga acacaatggt tgaggtgggc actaatgctg tcgctacgtt  2340
gaatcggtag atttaaatgg aagggagtgc aaagtagaa ttgggcaagt aatatgagtc   2400
ggtaaaggca gtaattctca cctgaacaaa gcatgaacaa caagtatac caatcagta    2460 aaaccaaaa aaaccaaaaa aaccaaaaaa taaaaaaatc gaaagtaaa agtatgattg    2520 gcatctggtg atggaggatc ccacaattta accttaggtc tcacatggaa agagggaaaa  2580
aaatttctgt ttacagtagg aagtgctcct tctcttatta ccataaatga gttcaacagt  2640
aaggaaatgg agggctgggt gtcacatggc agtcctcttc acttttgtca tagccttggt  2700
```

-continued

```
gatacaatta tacacacttt gaatgatgta agagatgaaa ataaatggag agagagagag    2760
ggaggagggt acgtggaagg gtggggtcat gtaaaatgga ggggccagga gacttcatat    2820
tttctaatga aaatttctag ctcagtgatc atccgaacca aaccttaaat gagctctgca    2880
gctatttgtc tcataataaa atccataata aaatccattg gatgtgattt catcacttga    2940
tatacatttg atttaaaaa gttaatttct tataacttat atttatactc cctccgtttc    3000
aatataaatg tcttactttc cattttggga tgtttcaaaa taagtgtcct attccaaaag    3060
tcaaagattc tttttagtc atttcctaaa ataccattaa aaggtattc tttcttttc     3120 taatattttg catacttgaa ggcaaaatta gaatttcaaa ataaatatat tgatgtgaaa    3180
acatttaaaa agattttctt aaaaaacgtg ttttttcaaa taagacactt attataaaac    3240
ggatggagta taagaatgca tcacagcaga tgaaatttta ttatgggtca aaagatataa    3300
cgtcaaattg cgttttccta actttagatg ttacaaaagt taactcaaca aaatgaaaaa    3360
aagcaagcat tattataaaa aaaaaaaaa aaatgatagg tcccttcatt ttattttttct   3420 ttcctacgct cattttgtat aaaggtttaa cctcatagga gtgcaactta gcctaacgtc    3480
tcattcaccc cattaataat cgattgcttt caaaagtccc tttcctctct ctcctctctc    3540
tctctctctc tctctctctc tgtctctcca atgcaccccc atcacacaca tgaaagagaa    3600 aaagggtta atggactctg aaatctgatg agtgattgtc ctctttagcc ttctcctttg     3660
gcttcttcat catacaaacc acccacaaag ctatacaaaa tatatagatt cacagagaga    3720
gagagagaga gagagagaga gagaggaata tatagtatat agaaaattaa gttggaagtg    3780
cttgataatg gatgaagggt catttctaac tttataaata cccatctctg agaactacgt    3840
ccttccattt tctgcttctc tctgtccaga tttgagagaa accaaggcag aaacctttgt    3900
ttccgtcctt aattatctcc ttcccggccc tttgtttctt caccaggtta gtaagctgaa    3960
aattggaaca tatataatct aaaatcattt tcaatgcttc accttctatg ggtcaatctc    4020 ttttttctc cttcgttttt ttctcacttc gaatcctgat tcaggcctat tgcttcgttc     4080
gttgatcacc gagaagtgta gaaaagaaa tgaaaacttg gaaatcttgt aacaaccaat    4140
cagctagtta catgattcca aaattttcat tctctttcta tgactttaca caaatattat    4200
aactttttgt taccgaatta acgatctgtt tgtgttttga ttcagctttc aaccacggct    4260
ttcgtaaacc aatcgaggga ggtatctccc cagagaaaaa tgggtagggg aaagatcgag    4320
atcaagcgga tcgagaacac gacaaaccgc caagtcacct tctgtaaacg gcgcaacggc    4380
ttactcaaga aggcctatga attatctgtt ctctgtgatg ccgaggtagc ccttatcgtc    4440
ttctctaccc gtggccgcct ttacgagtat gccaacaaca ggtcattgct tccctttcac    4500
tttaattttt ttcaatggat catgtcaaaa gctttacctt cttcttcaaa ggccttaatt    4560
tctttgttat ttaaagacta caattttttt taaagttaaa aataatgatg cccttcctgt    4620
ttatagttca gcttggatct gcagtagatc tttgagtgga tttaatcaca ggaacataat    4680 cattttatt ttattttatg tgaagtgaag attgagttct ctcttaacaa agattcactt     4740
gtctttcttt gttctgtttt gttttttttc ctctacaagc ctttttttt ctttctttt     4800 atgacccagt tttagtttat agtttggtgt atacatagat ctgttgtaat agatggaaat    4860
agaagcatta tggttgtgta ggagtaaaca agtagaggtt ttgggaaggt atgcaggtct    4920
gtgagatcag cctcctatct cctccattgt tgctaagttt tctgtttcct ttctcttttt    4980
ctccttttat tccacttgct ctctctctct ctctctctct ctctctctct ctcttttct    5040 ctctctccat tgtacatgtc atctatgaag agctacaaca aagctgtcat gctctcatta    5100
```

```
gcccattccc tcaatccccc ttgacacttc cttaatagca cgtcagttga acactacaca    5160
tcaagaaacc aaaaggacaa tgagaaaaat tgtcatgaac ccattaaaaa cggcatattc    5220
ttagggtttc ccaaaacccc ggtttctctt taaacatgtt aaacacactt ttaaagccaa    5280
tcacaatctc attaggttac aatcaataca accagaacta gggttttttt tttttcccca    5340
ccatcagcta gacgaaattt catggattat tggaacacat ggaagactac tttacagtca    5400
aacataacca aattaggttt tattagcaag tacatgggtc atggggtttg aattccaaga    5460
cttacatggg tatttcctta attattaaaa aaaaaattca agtgaaaaga ccatcattaa    5520
ccagccaatc aaaacccact tagggtttga cacgtacaag ggtctagttg gggtccaaga    5580
ccagatttgg tgggtttgtg gtttatctta gttacaagaa tctttggtca cgtcaccctt    5640
gattttttca cttgttgaac ttctgacaat agagtaatgt catgattcca acactgggtt    5700
tctctttatt tcatccgtcc atcaccaacc ctaaattttt tttatcttca aaggtgaaaa    5760 atacccctaat ggggagggtc acttcttcta cttagataga tctcttttag ctctctctct    5820
ctctctctct ctctctcttt ctctctctct ctgttcaccc tttcacaaag cgtctgaacc    5880
tgctgaagct gaaacagcaa agagagaaag agctcataca gagacatact gatggagagt    5940
gacgagccaa tcaaaatagc tcatctgggc caccttgtcc tgtctagggc atttgagagt    6000
gaggtttgta tttcttgaag atctttgcat agatatattt gtgtaataac actcactcat    6060
ctctttctct ctctagaaag atgagagaga gatatagata agatggtacg gcagctgaga    6120
cccaatggga gagttctgag catctgtggc tttctttatc atgcatgggt aaaaagagta    6180
caacattggc tgcctaaagt ggacggctct gatgtactca gagtttccca gacggaaaag    6240
acttatctct tttttttttt ataattgtga aagtacttgg cttccaatat tttaagggtt    6300
tagtaatttt cgaggtgggt aatagggaac ggtcatggat attatctatt gtgtaatggg    6360
tggatccgac acctggcgga gatctggcaa tggagattgt tcagccaatc ataggtgggg    6420
gagtcgtgcc agcatggcag agggaaccaa tcagtggctc gatgaaatta aggtagcagc    6480
acatcaagat caatggggtc ttttctcagc gcaatataat atataatatt taattagatt    6540
accatctcgt ggccttataa ctgagttagt ctgactcaca ttaaatcatg tgcttattca    6600
gtttcagttt tagatttacg tgttagggtc agttaactga gaaagttggt tgatttgacc    6660
gttaatatta gccatttccg tggctaatct catcttaatt tattatcatt aggtatcatg    6720
gtcatatgtc ttgtgtggcc ctacacgtgg ctaaaatcta gaccaataaa agagcttgga    6780
ctttagggat atatcttctc ttggttgtca caagtaattt tcacaactta gcaacaaaaa    6840
acaaaaaagt aattttcaca atccttctac atcctcccctt tttctttatt ttattttttt    6900
ctcttaattt tattttattt taaaattaa atgattaaag ctttaggggt actctagact    6960
ttattcttat taaggttttt ttgataatca ttcttattaa ggtttcagca tagacaaatc    7020 ccttttctt tcattgata tatatgtatt cactcaaaca cccccagaaa gaaaacccac    7080
atatgccaac accctcacaa tgattcgaac ccaaacgtga aataggatgc tcacatgtta    7140 tattttcga cctcagtggc atattttgtg tatctcaatc gattaaacta gatcttactg    7200
tatttagtac tacaagggac gtactatgca ggttagtgca attcttgaac ttctactaat    7260
gcttgttcta caattactac cttttgtgta tctcaatcaa ttaaattgga tcttatttgg    7320
atttagtatt agaagggacg tactatgcag gttggtactg caattcttga gctagttttt    7380
cttgttcttc aattactttta taaaatttta ggaatttgca agagaaatag ctagcctttg    7440
```

```
ggactgcttc tatcattagc cgtgagcttt ttaagagaac aataaaattc taatgttgta    7500
agatacattt gaatttagaa cttatttggt tagggtttag ttgaatttga taatacttga    7560
ttgaatacgt tcattacttt catatgaaac tgcctgtgat tttgtatttt tcccttatct    7620
ctgtataccg tgacagcttt ggtcttttga ataataataa ttggaaattt tgtccaaaat    7680
ttagtttaat gttttatcag ccaaaaatga ggggctatg atttgcttat tttgatctaa     7740
gcgtattgca ttatttcctt cttaataaag tgtcgatttt tctgattata ataacatac    7800
taatgtgaag ataattttta atttgctgga cctagttttcc acgttgcact atgcaagaat  7860
gaccgcgatt gccactaaaa tgatttctaa aagattattt ttatttattt ctagggacga    7920
atatgtgaag gacaagaata caattcttag ggatgtaaat ctcacatatt tttcttgcat    7980
aatccaagaa acattatatt agtctgccat tgaagtttaa ataaggaatt aagaaacatt    8040
atactatcga agcattaaca ctacaatgat atccatagta aagtgtttga agtggtgatt    8100
taatggtaat ctgagcaatg ttttttgtttt ttcttgcccc tacaaatttc gtaaattgtt   8160
tccattcata caaatgttga tacacatttg gcatcacttc taaatgcttg atgttatagt    8220
gattcaaagg ttttagtgaa gaactattat tttcattgct agtttctgga tcctgtgaaa    8280
ttaagaaatg tggtagtgaa aaatcattgc taactttaat atttattaaa gtgtgataat    8340
ttattagtca attggtatgg aaattgtaaa aggcaattta ggtaatgaag aatgttatta    8400
tacttcacta aatgaacaaa gatgtttagg ctatcatatt tataattaag catcaaacta    8460
cagcttaaaa cagagggaaa acacccccccc ccacccacat aaaaaaaaaa aaaaaaaaa    8520
agagagagaa agaaagaaag aaagaaagac agaaagaaaa ggataaagta gacctatata    8580
agtatgctta acctgaaaag ggggtttttt tggctttgat tgtaatcttc ccacacttaa    8640
attaagttca cttaaactgg gcaagttgca aaagacatga acataagatt cttcgctgct    8700
ttcagcttct tacaatagaa aattatcttt tctagaaata ataaataatg cttcttatta    8760
atattctttc ttatggaact tcatgctgct tttgaatcct aagttttaat tgatacttta    8820
aacaaaaagt taaaacggtc ctgcaagttt gaaacatgat gatcatctgc agtcttttaa    8880
tatctttact taaactgtat gaaatatttg cgtttcattt aaacttaccc ccacagcgta    8940
gctactagct agaccacttg gtcattggca ccattccatc tacagcagtc ctagcattaa    9000
ttttgatttt tcttgatgct tgtttcttca ctcattaaca attctgtctt tcttgatgaa    9060
gatattcatt atgggatgat cgacatgtta caataagagt tgttcgtaag taaatcactc    9120
gatcaacata taattggacg ttttattgac cacttcatca gatagaagga agttgagatt    9180
cagatattat ttggacttcg agtaactccc aatatgtaaa aaagtagggt aattactgat    9240
taaaaaattt agcaagaatc tgagtgtaac taggagatag gggagggaaa ttgggtggaa    9300
cataatgcat gttgttttga aatagtaaca taaaattgac atttatgacc tgagataata    9360
tatctcccct ctttcttaca atattagaca taatttcttc tacttcatat tcatcaagat    9420
ttctctagga aatagatcaa ctcccttccg cccaaacctt ttaatcatgc attaacgctc    9480
tgtttaatgt tttggaataa gtaaattgta tggttctaga agaccctcaa aactgttatt    9540
cttgaatcac aaaattctttg ttaataaaag tcgtgcattt cttgaaaatg acttccactt   9600
tgttttttga gatgccattt tacaagaaat taaataggct ggacagtaga caccaacttc    9660
attcacctca tgatcatatg atcacaatga tacaaagcct catccgatgg cattagcaat    9720
tacatgattt caatctaagt atttttttttt tcctataaaa ttttcaatcg gcgaaccaat    9780
agggcaatgg gggtctatgt gaaccaagc attgattgag gtaattttcc taaaaataaa     9840
```

```
ttatttttgc ttcttcttcc ctttgttttt tttttttaaa aaaaaagaaa gagagaaaag    9900
gatagatcaa gagctcatac agaattatgc ataaactttt ggtttaaaac agatgtcacg    9960
gcagtaatga tggtgtcttt atcatatacc atcagctggt actttatctt ctgatatgtg   10020
aaaatatata tatatatata tatatatata tatatatact agatatagca cacgtgcgtt   10080
gcacatgaat atttttaaat aatattatag gtagtataga ttagttattt tgtatattat   10140
aggtagtata gattagttat acagaataat aaatacataa agattttata ttttttaata   10200
aaagacaaat tttaaaattc aaaagtacat ttattattat tatttataat ttataatcaa   10260
aattgttaat gaaagattaa aaacttttag atatacattc agaatttttt tttcttcata   10320
aaacggaata tttaaagagt ttatattcat atatattatg caacttgata gttgctctag   10380
gaaaaaaaat ttgagtaaga atcaacttt aatttgttaa gagtttgagt taaaatctaa    10440
ctttcatttg ttatcaaatt ataagaatat ttactatgtg tttcaattaa agaatggta    10500
gatatgtatt tttttttat aaaaaaaata agggtatatt ggttgtttaa agttttttt     10560
gagattcagc cttttatagg tagtatatat atatatgttc aaagattccc ctaagtgaac   10620
cctagcttct tgtgttttga actcaaaata actttttct gcctttgttt atctatcttt    10680
cttcatcata aaatataaag ctcttccaaa aaggtcaaa tacaattttt ttcaataacc    10740
tagacaataa taatcatcgc agcatacttg aattacttca aatacatgca aaattttcca   10800
attctgtgcg agcttgcatg cgtgtgtatg tttgtgtgtg ttttgttgtt cattttatt    10860
gttgtgtgtg tgcgtgcgtg tgtgtgtgtg tgtgggtttt ttttttttg gtaaaatcag    10920
aaaaaggatt ttattaagag aaatgggatt acaacctaca aatcagtaaa gaaagcaacc   10980
cccaccataa ttcatgaaat acaagatcga agacaaaccc cactaagaac aaaagaaacc   11040
aaccccccaat acatgataat taatcacaaa acccagccta agaagagccg gcagaataga  11100
aattacctca ggtcagacac aaaactgtac tcatagagca aaattatatc acaatcagta   11160
cataaagcaa aattattgga cccaatagat gaagaatcat atgaacttat ctgcacaaag   11220
ccaagtagca ttggcaccac aagaaccctc catcaaggta cagatgaaaa cctgctagac   11280
aaaaccagca agaataactc tagaaacccc acataacttc cttctagttt gttctacatc   11340
taggtcaatg ttaaaagttt gcaatgtcta ttttgtattt attaaaagtg aaatatctca   11400
gcaagtatcc aatagtccta agttgagcat attcaccaag aacatttgac atagaaactg   11460
tttacctttt tcaaaacttt taatttcatg acttttgcaa cacaccgtac tgaggaaatt   11520
tatttatgtt gctgatcacc ctttttagg ttggtagctg acacttgagg tgacccttct    11580
aaggggctga tttcatgtta aagggcttg atgttagata gtgcaatgga acttccgaac    11640
ttagctatat cactttgctg gcttggtgga taggtctaaa attggaagca gccctggta    11700
gaggcacctc accctttagg gcaatttgtt caacctatac ttgaagaact tcatcaaaat   11760
tttcagcaac atatttacga tcaaaacttt actccgtacg aattatatta gctactggct   11820
attaacccat tatgaagtct tctctctctc tctctctctc tctctcgata tatgtatata   11880
tatatatata tttatatata tatatatata tatatatata tatatgggtg atgatctggt   11940
aagcacgtag gagttgtact ttgtgcatta atgggatatg aggtacattg gactaatgta   12000
agaggtataa cccctaatgt atagtgctga tataacttat atcaatacgc gctgatggga   12060
acataactga tatatatata tatatatata tatagaaaat atcatttcac catgagaata   12120
tgaccatatc aataagcgtg tttgtgccac atcatgtgtc tgtatactat tttgttgggt   12180
```

```
aaaatacagt tttgaagaat tgacaaaatt atgtgaaaca gccttgaata ggttgatagt    12240
gttgacgtca accatatttta tagtcaaatg gccccaaagt attactgtta cccttattaa    12300
tttgtttatt tttgggttta accggggtac tgctgtcctt tttgatgtgc ataatgaagc    12360
atttttctac cactcctacc aaattacctt atgacttccc agaatgctaa ggaaagatat    12420
agagacaaac ctagtaccca cccaagatct tgacaacaat attatcaatc aaagctaagt    12480
tagtatccac ctaagacctc accaatttat ttgaatttta gcagcttatg gtagggttaa    12540
acaggcaacc ttatggtagc tgggctcaac aatataatta atgatttcaa ttccacctgc    12600
ctaatagtac attcaaaggc tttaagtttc agttttagaa acattatcag tcctcgtaaa    12660
attgtaacaa aggataaaaa taaaataaaa ttgtgttaaa tacctgatac gttgataaaa    12720
gaattgtcaa aattgtatga attggttgaa gaagaaaaaa tattgtagtt tggttgcaat    12780
ttagtgactg ttatattggt gctagccttt tgtatcacta ttgcctcttc ctcatataat    12840
tataatatga aaactatat atatatatat atgctgatgt tttgaagttg cttgttaagt    12900
gtgctcgact gatttgaaat gcagcacttt ttatagcagt catatcatta atattatgat    12960
ttttcagtgt taaagcaaca attgagaggt ataagaaggc atctgtggat tcctccaata    13020
ctggatctgt ttctgaagcc aatgctcagg tacactggtt tctacacgta taaactttta    13080
gtgacatgga cgctgaataa accattacat cataacctgt agtcacatgt ccacttgaag    13140
gaaagttgag tcatgtagtc ctgacttttt ctaatgtggc aaatggtcag ttgttagttt    13200
actctatatg gaaatgtgag aaatatagat ttaatacttc gggtgacaaa acttaaggca    13260
ggacttcaga aactgaaata tctgcatcag ctctagaatg tcttagaaat tagaattcat    13320
ggaaatcatt caaggaattt tgtaatggat acggattttc atttggaaac tataatagaa    13380
taattctcgg cattatttat gaccgatcaa ttagaatgat cttgagtgta gtacgtgata    13440
aattcaagaa taaactacaa ttaactaaaa aaggaaaaaa atggaaaatg aaaaaacaag    13500
ataataatgc tgatacaact ttgggaactt ttttagtttc acagattgtt acctttttttc    13560 tcaataagat attctgacaa caatgatatg tgggcataca tctcagttct accagcaaga    13620
agctggcaaa ctgcgtaacc aaatcaggaa tatgcagaat acaaacaggt atttcaaaga    13680
atattcatca attacatttt agtaaaaatt tcggaattaa cctttttattt aacaatgcta    13740 ttttcaggac tatgctgggt gagtctttgg gctctctgag tcccaaagaa ctcaagggtc    13800
tggagactaa attagagaaa ggcattagca aaataaggtc caaaaaggta tcaattgcct    13860
catcaatact atacatccat gaatgtttct tatagtctct atataaattc tgtttctggt    13920
tgcttctggc tcattgcata cctctgacaa gggtttcttt atttcctttt ttttttttcg    13980
caaatgctac cagaatgagc tactgttttc cgaaattgaa tacatgcaaa agagggtaac    14040
tatttctact cttgttcttg ttcctcgttg atgttacaac atactagaat atgctactgt    14100
ttacttgatt tcaatatcag ctagtacggc ccatgtcatt ttgaaatata tatagcaggc    14160
agcctctttg acctccttgt aacatctttg aacgtacacc aaacagagaa aggatgagtg    14220
ataaacatga catagatgtt aaaaatccta ataaaaaata aaaataaaa aataagcaag    14280 ttgcatcttc ataactgcat ctcagctaga agctaaggtt cttgagcagt ttatactgca    14340
aaactaccac attgtttatt tgaccctgtt gatctgattg tgcttttttc ttccaatttt    14400
gaaagaacat tgcaataata tggcagcaaa aatgtaattt ttttagtgt tcagtattga    14460 aatgtgatca catttcttcc tcctaatgtt gctctcattc tcatgatagc taaaatttgt    14520
attgcaggaa atcgacttgc acaatgataa ccagtatctc cgagcaaaag tctctctctc    14580
```

```
tctctctctc tctctctctg tctaaatagt aataatatta atatttttg tggaaagtga    14640 ctgattgaac atagcttttg tgaatggtgt agatagctga acacgagaga gctcaacagc    14700
aaatgaactt gatgccaggt ggatcaaact atgaggtctt gccatcacag ccatttgact    14760
ctcggaactt tttccaagta aatgcattgc aacccaatca tcattactct cgccaagatc    14820
aaatggccct tcaattagtg taagaatttc tcgacattta tgccatcata aatcatcaaa    14880
gacctaaaca tgcatactaa ctatatacat tgggtgtaat agtttgatat gcatttccca    14940
ttgttcatat ttttaatgga tttcaccaag tcgaagtaca tagaagaagt aacaattgac    15000
atgaaaatca caccaaatag gctgattgat cggtgacatt ttctaggaca aattgtttca    15060
aattctattt gattatcaca acctatcaat ccattcaaac atgttggttg ttgaattggt    15120
ctattttgtc ctacgaattt gtcaattgat ccattgaata ctagttgtgt tttatgtagg    15180
atactagcag cttgcacccc actagattgc ttattaaatt gtacacttat attagaggtt    15240
taattgcttt gtcaatattc tttctaatta ctcgaatgtc ttcttaataa ttttcaagtt    15300
aaaacccaat tacaacatat ttggaaaagt atgacccaaa cctgcgaacc cattttgtca    15360
aatcggtgtt gatttggctt gcagaccaga acatctttaa acattaactt tttattttt    15420 aaattaaaag actttaattg aacttcttat aataattaca ataattttg tggcttggga    15480 gccagtttgg tagtttcgaa tgtgataaat tcagtataac ttgactactt gagccatgtt    15540
ctcacacatg gactattgta ctacagctca tgcaagatga tcccctgatg tgcaagtaat    15600
ctccatgtag gctgttctat catggtgcat aactccacgg ctccaatgcc aaaatgatag    15660
tataatctca agaatttgcc taaccttttt cttttatttt ttttcctgta ttttctgtgc    15720
agttaatggg cctgaaggag agctaatatc tactttgttt atattctgtg gaaggaatat    15780
actattctac cagattaagc tatgtgtaag ttgggataaa agcagtgacc aaactgtatt    15840
ccagtggagg gctttagtat tctctgatgg gttgttagct tcttagaaga tcataagact    15900
cctaacaatg ttattagcta gtgaaagaca tcttttctgt atgttttatg caagcactac    15960
catgctataa cagatactac ttatgtattt cttatgcttt gtgtgatttt gtctctgtct    16020
tgtcctcgtt aaatttgctt gcatgttgcc tttaagcatt gttagctaaa ttatgttgtt    16080
tctgtgagtt caaatctttg aacaaaattt agggcttaca aaccatggag aaataatagg    16140
tgcttatcgt tgctgctcct agatagtccc tacctgggga aaggatcaga ggtagtgccc    16200
ccaaatccct gttttgaggc attaggcata taaaagaaga tatactctaa tgacaaataa    16260
aatttatatc ctgcaacttc tatatggaaa actaatagct agtaaaattg agttgttttt    16320
ggcactatct agctgcgtca gaaaatctct acaagtcttg ggtgaaagcc ttctagggtt    16380 tcctttgca ctttgtcatt atcataccttt caaatatagt tgttattaaa aaccaatgtt    16440
ttctcctatc ttttttctca tttttttgga tgaaggccag actgttaaac cgcccactga    16500
acaactttac aattatgtgc ttggaagtag gctaaaaatg aggatgaagg caccctttt    16560 gtcagatgag aatcaaattg caagctgtga agggagctt tctttgggt tgtagtcttc    16620 atatacaaag gccagatcca ggccttaaga tgtggaaagc caaaaaaat taggtaccca    16680 aaaaaatcat accattcgta ggaggaatgc taatctgaca ctgtacttcc tagttggtta    16740
gactgtcatc atagctgact ccactttgca atcttttccc cttatcaacg aaaatttttt    16800
tttctattgt tggggaaaaa aagaaaaaa agaaatgcg tgtgatatgg gtctccttcc    16860
catttcatct acattcaagc agttcaagag catacctatt tcctgataat gcctactcaa    16920
```

```
atcttataga acgttgagct aggcatttga ctaagacatt atacagcaag gttttaaca      16980 ctatcgtatc acattctatt taattggtgg acgtagtttg actctggtac atagaatcaa      17040
gtatatatat gtttcagtga catgcaaatt attcactact ataaagaact tgcgaaaaac      17100
cttcaagctt tttgttccag aatgattcat gaatgacatc gtatgcatgt ttcttttttcc     17160 taagatgcat ggcttttca cattcctgga ttcatttttt taattacttc ccgaatttca       17220
tcttcttcca catgccaaat aattcatgaa tttcaaggct gctccatgtg ttgtaatgga      17280
aatcattttg tagctgaaaa tttgctgtca ttggttttaa ctttcaagta aacaattgcg      17340
tgtttcattg gtaagatttt tatgtggcct cattttggta gataacttct taccaaaaaa     17400
aaaaaaaagg cacacaatct cgtttccaca tcgatctttt gcagaacatg aagagaaaca     17460
caacattcac cacttactgt atcacaccct ttccacatcg atcttttcct aagtactccc      17520
tttgtacgtg tcactatagc tagcctgcat ggctgcattt ccttccttaa aactgagcta     17580
ggtggttgat atcatatggg tgagcatcag atgggcttgg agcattgtag tatttgtgtc     17640
cagtgatcga gaattc                                                     17656
```

```
<210> SEQ ID NO 4
<211> LENGTH: 21
<212> TYPE: DNA
<213> ORGANISM: Liquidambar styraciflua

<400> SEQUENCE: 4
cttgtgacaa ccaagagaag a                                                21

<210> SEQ ID NO 5
<211> LENGTH: 23
<212> TYPE: DNA
<213> ORGANISM: Liquidambar styraciflua

<400> SEQUENCE: 5
ttattaaggt ttcagcatag aca                                              23

<210> SEQ ID NO 6
<211> LENGTH: 23
<212> TYPE: DNA
<213> ORGANISM: Liquidambar styraciflua

<400> SEQUENCE: 6
tatggtgttc cttttcata ctc                                               23

<210> SEQ ID NO 7
<211> LENGTH: 22
<212> TYPE: DNA
<213> ORGANISM: Liquidambar styraciflua

<400> SEQUENCE: 7 aacttttat ggcacaacaa ga                                                22

<210> SEQ ID NO 8
<211> LENGTH: 23
<212> TYPE: DNA
<213> ORGANISM: Liquidambar styraciflua

<400> SEQUENCE: 8
caatcccttc acatttactg aga                                              23

<210> SEQ ID NO 9
<211> LENGTH: 20
```

```
<212> TYPE: DNA
<213> ORGANISM: Liquidambar styraciflua

<400> SEQUENCE: 9
ttagctcagg ggaggtgaac                                           20

<210> SEQ ID NO 10
<211> LENGTH: 21
<212> TYPE: DNA
<213> ORGANISM: Liquidambar styraciflua

<400> SEQUENCE: 10
cctttttgca ggtcaatgtt c                                         21

<210> SEQ ID NO 11
<211> LENGTH: 20
<212> TYPE: DNA
<213> ORGANISM: Liquidambar styraciflua

<400> SEQUENCE: 11
gtgggtatgg aacagtgaca                                           20

<210> SEQ ID NO 12
<211> LENGTH: 23
<212> TYPE: DNA
<213> ORGANISM: Liquidambar styraciflua

<400> SEQUENCE: 12
tgcatgggta aaagagtac aac                                        23

<210> SEQ ID NO 13
<211> LENGTH: 23
<212> TYPE: DNA
<213> ORGANISM: Liquidambar styraciflua

<400> SEQUENCE: 13
aacatcttgt tcatttagtg aag                                       23

<210> SEQ ID NO 14
<211> LENGTH: 21
<212> TYPE: DNA
<213> ORGANISM: Liquidambar styraciflua

<400> SEQUENCE: 14
gctatgacaa aagtgaagag g                                         21

<210> SEQ ID NO 15
<211> LENGTH: 20
<212> TYPE: DNA
<213> ORGANISM: Liquidambar styraciflua

<400> SEQUENCE: 15
ctctgcagct atttgtctca                                           20

<210> SEQ ID NO 16
<211> LENGTH: 22
<212> TYPE: DNA
<213> ORGANISM: Liquidambar styraciflua

<400> SEQUENCE: 16
gattattaat ggggtgaatg ag                                        22

<210> SEQ ID NO 17
```

-continued

```
<211> LENGTH: 20
<212> TYPE: DNA
<213> ORGANISM: Liquidambar styraciflua

<400> SEQUENCE: 17
ccgttacaga aggtgacttg                                                  20

<210> SEQ ID NO 18
<211> LENGTH: 22
<212> TYPE: DNA
<213> ORGANISM: Liquidambar styraciflua

<400> SEQUENCE: 18
caatgctatt ttcaggacta tg                                               22

<210> SEQ ID NO 19
<211> LENGTH: 21
<212> TYPE: DNA
<213> ORGANISM: Liquidambar styraciflua

<400> SEQUENCE: 19
ttcctcctaa tgttgctctc a                                                21

<210> SEQ ID NO 20
<211> LENGTH: 22
<212> TYPE: DNA
<213> ORGANISM: Liquidambar styraciflua

<400> SEQUENCE: 20
caacctatca atccattcaa ac                                               22

<210> SEQ ID NO 21
<211> LENGTH: 23
<212> TYPE: DNA
<213> ORGANISM: Liquidambar styraciflua

<400> SEQUENCE: 21
aaaaaccaat gttttctcct atc                                              23

<210> SEQ ID NO 22
<211> LENGTH: 22
<212> TYPE: DNA
<213> ORGANISM: Liquidambar styraciflua

<400> SEQUENCE: 22
attcatgaat gacatccgta tg                                               22

<210> SEQ ID NO 23
<211> LENGTH: 22
<212> TYPE: DNA
<213> ORGANISM: Liquidambar styraciflua

<400> SEQUENCE: 23
cttgaaggtt tttcgcagtt ct                                               22

<210> SEQ ID NO 24
<211> LENGTH: 20
<212> TYPE: DNA
<213> ORGANISM: Liquidambar styraciflua

<400> SEQUENCE: 24
ctaggagcag caacgataag                                                  20
```

-continued

<210> SEQ ID NO 25
<211> LENGTH: 22
<212> TYPE: DNA
<213> ORGANISM: Liquidambar styraciflua

<400> SEQUENCE: 25
ttaactgcac agaaaataca gg                                              22

<210> SEQ ID NO 26
<211> LENGTH: 22
<212> TYPE: DNA
<213> ORGANISM: Liquidambar styraciflua

<400> SEQUENCE: 26
caaaagctat gttcaatcag tc                                              22

<210> SEQ ID NO 27
<211> LENGTH: 20
<212> TYPE: DNA
<213> ORGANISM: Liquidambar styraciflua

<400> SEQUENCE: 27
ttcgcaggtt tgggtcatac                                                 20

<210> SEQ ID NO 28
<211> LENGTH: 21
<212> TYPE: DNA
<213> ORGANISM: Liquidambar styraciflua

<400> SEQUENCE: 28
ggtatgataa tgacaaagtg c                                               21

<210> SEQ ID NO 29
<211> LENGTH: 21
<212> TYPE: DNA
<213> ORGANISM: Liquidambar styraciflua

<400> SEQUENCE: 29
gatgtggaaa cgagattgtg t                                               21

<210> SEQ ID NO 30
<211> LENGTH: 22
<212> TYPE: DNA
<213> ORGANISM: Liquidambar styraciflua

<400> SEQUENCE: 30
tcatgctgct tttgaatcct aa                                              22

<210> SEQ ID NO 31
<211> LENGTH: 21
<212> TYPE: DNA
<213> ORGANISM: Liquidambar styraciflua

<400> SEQUENCE: 31
acagatgtca cggcagtaat g                                               21

<210> SEQ ID NO 32
<211> LENGTH: 21
<212> TYPE: DNA
<213> ORGANISM: Liquidambar styraciflua

<400> SEQUENCE: 32
agaggtataa gaaggcatct g                                               21

-continued

```
<210> SEQ ID NO 33
<211> LENGTH: 22
<212> TYPE: DNA
<213> ORGANISM: Liquidambar styraciflua

<400> SEQUENCE: 33
cattggcttc agaaacagat tc                                               22

<210> SEQ ID NO 34
<211> LENGTH: 23
<212> TYPE: DNA
<213> ORGANISM: Liquidambar styraciflua

<400> SEQUENCE: 34
ggttggtttc ttttgttctt agt                                              23

<210> SEQ ID NO 35
<211> LENGTH: 22
<212> TYPE: DNA
<213> ORGANISM: Liquidambar styraciflua

<400> SEQUENCE: 35
gaataacagt tttgagggtc tt                                               22

<210> SEQ ID NO 36
<211> LENGTH: 23
<212> TYPE: DNA
<213> ORGANISM: Liquidambar styraciflua

<400> SEQUENCE: 36
ttdccattgc actatctaac atc                                              23
```